(12) United States Patent
Bisht et al.

(10) Patent No.: US 8,236,853 B1
(45) Date of Patent: Aug. 7, 2012

(54) FORMATION OF CYCLOPENTENE NITRO-ESTER AND DERIVATIVES

(75) Inventors: Kirpal S. Bisht, Tampa, FL (US); Pasha M. Khan, Tampa, FL (US); Alberto van Olphen, Tampa, FL (US); Ruizhi Wu, Tampa, FL (US)

(73) Assignee: University of South Florida, Tampa, FL (US)

( * ) Notice: Subject to any disclaimer, the term of this patent is extended or adjusted under 35 U.S.C. 154(b) by 731 days.

(21) Appl. No.: 12/327,410

(22) Filed: Dec. 3, 2008

Related U.S. Application Data

(60) Provisional application No. 60/991,895, filed on Dec. 3, 2007.

(51) Int. Cl.
*A61K 31/21* (2006.01)
(52) U.S. Cl. .......................... 514/546; 435/132; 435/135
(58) Field of Classification Search .................. 435/132, 435/135, 155, 197; 514/546
See application file for complete search history.

(56) References Cited

U.S. PATENT DOCUMENTS

| | | | |
|---|---|---|---|
| 5,714,351 A | 2/1998 | Evans et al. | |
| 6,137,007 A | 10/2000 | Bernegger et al. | |
| 6,368,850 B1 | 4/2002 | Bernegger-Egli et al. | |
| 6,448,051 B1 | 9/2002 | Bastawade et al. | |

FOREIGN PATENT DOCUMENTS

| | | | |
|---|---|---|---|
| WO | 0058500 A1 | 10/2000 | |

OTHER PUBLICATIONS

Johnson et al., Pure and Applied Chemistry 64(8), 1115-20 (1992).*
Berkowitz et al., Tetrahedron: Asymmetry 7(6), 1577-1580 (1996).*
Uenichi J.; Hamada M. "Stereospecific substitution of enantiomerically pure 1-(2-pyridinyl)ethyl methanesulfonate with beta-dicarbony compounds." Chem Pharm Bull. Tokyo. 2002. May. vol. 50. No. 5. pp. 697-700.
Petersen M.; Kiener A. "Preparation & Functionalization of N-Heterocycles." Green Chemistry. Apr. 1999. vol. 1. No. 2. pp. 99-106.
Schmid A.; Dordick J.S.; Hauer B.; Kiener A.; Wubbolts M.; Witholt B. "Industrial biocatalysis today and tomorrow." Nature. Jan. 11, 2001. vol. 409. No. 6817. pp. 258-268.
Khan Pasha M.; Ruizhi Wu; Bisht Kirpal S. "Pd(0) catalyzed intramolecular alkylation : stereoselective synthesis of furan and isoxazoline-2-oxide analogs." Tetrahedron. 2007. vol. 63. No. 5. pp. 1116-1126.

* cited by examiner

*Primary Examiner* — Chih-Min Kam
(74) *Attorney, Agent, or Firm* — Robert Varkonyi; Smith & Hopen, P.A.

(57) ABSTRACT

Disclosed is a method of synthesizing new optically pure heterocyclic compounds using Pd(0) catalyzed intramolecular cyclizations. Analogs of cyclopentanes, like isoxazoline-2-oxide and furan, with similar framework to the cyclopentanes act as anti-HIV and anticancer agents which opens a whole new field for application of these compounds. Starting from a meso-diol, optically pure compounds were prepared without utilizing chiral ligands at any stage of the synthesis. The stereochemical outcome of the product (>99% ee) was influenced by desymmetrization catalyzed by *Pseudomonas cepacia* lipase and the stereoselective nature of the palladium catalyzed transformations.

18 Claims, 12 Drawing Sheets

A

9, 13 : R$_3$ = Me ; 10, 14 : R$_3$ = Bu ;

11, 15 : R$_3$ = C≡C-Ph ; 12, 16 : R$_3$ = C≡C-SiMe$_3$

B   Dicyclopentadiene

| Compound | $R_1$ | $R_2$ | $R_3$ | Diastereomeric ratio | Yield |
|---|---|---|---|---|---|
| 17a | $NO_2$ | $CO_2Et$ | H | 1.07:1 | 62 |
| 17b | $NO_2$ | $CO_2Et$ | Me | 1.12:1 | 70 |
| 17c | $NO_2$ | $CO_2Et$ | Bu | 1.11:1 | 72 |
| 17d | $NO_2$ | $CO_2Et$ | C≡C–Ph | 1.13:1 | 60 |
| 17e | $NO_2$ | $CO_2Et$ | C≡C–SiMe$_3$ | 1.15:1 | 68 |
| 17f | COMe | $CO_2Et$ | H | 1.04:1 | 68 |
| 17g | COMe | $CO_2Et$ | Me | 1.28:1 | 65 |
| 17h | COMe | $CO_2Et$ | Bu | 1.19:1 | 70 |
| 17i | COPh | $SO_2Ph$ | H | 1.07:1 | 68 |
| 17j | COPh | $SO_2Ph$ | Me | 1.15:1 | 71 |
| 17k | COPh | $SO_2Ph$ | Bu | 1.13:1 | 73 |
| 17l | COPh | $SO_2Ph$ | C≡C–Ph | 1.06:1 | 61 |
| 17m | COPh | $SO_2Ph$ | C≡C–SiMe$_3$ | 1.10:1 | 69 |
| 17n | CN | $CO_2Et$ | H | 1.05:1 | 60 |
| 17o | CN | $PhSO_2$ | H | 1.23:1 | 68 |
| 17p | $CO_2Me$ | $CO_2Me$ | H | – | 73 |

Bases used: NaH, K2CO3, KtOBu
Pd(0) catalysts used: Pd(PPh3)4, Pd2(dba)3

| Compound | R1 | R2 | R3 | Yield[a] | $[\alpha]_D^{20}$ (CH$_2$C$_2$) |
|---|---|---|---|---|---|
| 19a | – | – | H | 85 | −95.2 |
| 19b | – | – | Me | 64 | −90.4 |
| 19c | – | – | Bu | 70 | −88.3 |
| 19d | – | – | C≡C-Ph | 63 | −182.3 |
| 19e | – | – | C≡C-SiMe$_3$ | 67 | −177.2 |
| 19f | Me | CO$_2$Et | H | 85 | −77.8 |
| 19g | Me | CO$_2$Et | Me | 57 | −148.1 |
| 19h | Me | CO$_2$Et | Bu | 55 | −258.8 |
| 19i | Ph | SO$_2$Ph | H | >98 | −20.0 |
| 19j | Ph | SO$_2$Ph | Me | 59 | −16.7 |
| 19k | Ph | SO$_2$Ph | Bu | 62 | −10.0 |
| 19l | Ph | SO$_2$Ph | C≡C-Ph | 65 | −15.0 |
| 19m | Ph | SO$_2$Ph | C≡C-SiMe$_3$ | 64 | −20.1 |
| 19n | CN | CO$_2$Et | H | −[b] | − |
| 19o | CN | SO$_2$Ph | H | −[b] | − |

FORMATION OF CYCLOPENTENE NITRO-ESTER AND DERIVATIVES

CROSS REFERENCE TO RELATED APPLICATION

This application claims priority to currently pending U.S. Provisional Patent Application No. 60/991,895, entitled "Formation of Cyclopentene Nitro-Ester and Derivatives", filed on Dec. 3, 2007, the contents of which are herein incorporated by reference.

FIELD OF INVENTION

This invention relates to methods of generating bicyclic dienic ethers and isoxazolines. Specifically, the invention provides for use of the enzymatic and chemical catalysis to generate optically pure bicyclic dienic ethers and isoxazolines.

BACKGROUND OF THE INVENTION

Furan compounds are cyclic dienic ethers, manufactured commercially through decarbonylation of furfural over palladium/charcoal. Furan and isoxazoline derivatives belong to important classes of pharmacophores found in a large number of natural products and are present in many therapeutic agents (Chen, I. J.; et al. *Planta Med.* 2006, 72, 351; Faulkner, D. *J. Nat. Prod. Rep.* 1984, 1, 251; Usui, T.; et al. *J. Antibiot.* 1971, 24, 93; Bindseil, K. U.; et al. *Helv. Chim. Acta* 1991, 74, 1281; Sakai, R.; et al. *J. Am. Chem. Soc.* 1997, 119, 4112; Encamacion, R. D.; et al. *J. Nat. Prod.* 2000, 63, 874; Fattorusso, E.; et al. *J. Chem. Soc.*, Chem. Commun. 1970, 752; Faulkner, D. *J. Nat. Prod. Rep.* 2002, 19, 1; Benharref, A.; Pais, M. *J. Nat. Prod.* 1996, 59, 177; Nicholas, O. M.; et al. *Org. Lett.* 2001, 3, 1543). Furan derivatives have been used as a building block for a large number of heterocyclic substructures and also as synthons in natural product synthesis (Wright, D. L. *Prog. Heterocycl. Chem.* 2005, 17, 1). These compounds are important forming components of lacquers, resin solvents, agricultural chemicals, lubricating oils, wetting agents, plastics, cements, and pharmaceuticals. Furan is also a precursor of tetrahydrofuran, which is a valuable solvent and itself a precursor to pyrrolidines and thiolanes. Isoxazoline derivatives also have great biological importance, for example, many GPII/IIIa inhibitors and human leukocyte elastase (HLE) inhibitors also have an isoxazoline skeleton (Mousa, S. A.; et al. *J. Cardiovasc. Pharmacol.* 1998, 32, 169; Groutas, W. C.; et al. *Bioorg. Med. Chem.* 1995, 3, 125). Isoxazoline derivatives have also been incorporated in fullerenes rendering special properties as nanoscale connectors in molecular electronic devices (Lee, H. M.; Lee, C.; Cho, M.; Hwang, Y. G.; Lee, K. H. *Bull. Korean Chem. Soc.* 2004, 25, 1850). Because of the importance of furans, significant research has been undertaken to develop more efficient processes of generating furan compounds.

The use of palladium catalysts in carbon-carbon and carbon-heteroatom bond forming reactions has been of great synthetic utility (Tsuji, J.; et al. *Tetrahedron Lett.* 1965, 6, 4387; Trost, B. M.; Fullerton, T. J. *J. Am. Chem. Soc.* 1973, 95, 292; Trost, B. M.; Crawley, M. L. *Chem. Rev.* 2003, 103, 2921; Hegedus, L. S. *Transition Metals in the Synthesis of Complex Organic Molecules*; University Science Books Sausalito, Calif., 1999; Li, J. J.; Gribble, O. W. *Palladium in Heterocyclic Chemistry. A Guide for the Synthetic Chemist*; Pergamon: Amsterdam and New York, N.Y., 2000; Vol. 20; Nicolaou, K. C.; et al. *Angew. Chem.*, Int. Ed. 2005, 44, 4442; Zeni, G.; Larock, R. *Chem. Rev.* 2004, 104, 2285). For example, palladium(0) catalyzed reaction of dimethyl (Z)-2-butenylene dicarbonate with dimethyl malonate led to formation of the (R)-dimethyl 2-vinylcyclopropane-1,1-dicarboxylate (compound 1), seen in FIG. 1, though in low enantiomeric excess (67%; Hayashi, et al. *Tetrahedron Lett.* 1988, 29, 66). The reaction of methyl acetyl acetate or acetylacetone with 2-butenylene dicarbonate, which led to formation of a trisubstituted furan derivative (compound 2), seen in FIG. 1, was also observed. The formation of compounds 1 and 2 has been rationalized through a nucleophilic attack of the enolate carbon leading to the C—C bond formation in 1 and the enolate oxygen leading to the formation of the C—O bond in compound 2 (Hayashi, et al. *Tetrahedron Lett.* 1988, 29, 66). In another example of the carbon heteroatom bond formation, the formation of compounds 3 and 4, seen in FIG. 1, was reported through Pd(0)-mediated alkylation (Yoshizaki, et al. *J. Org. Chem.* 1995, 60, 2016). The formation of isoxazoline-2-oxide, compound 5, upon reaction of lithium [(phenylsulfonyl)methylene]nitronate with cis-1,4-diacetoxycyclopent-2-ene in the presence of Pd(0) catalysts, seen in FIG. 1, was observed (Trost, B. M.; et al. *J. Am. Chem. Soc.* 1992, 114, 8745). However, these present methods suffer from the ambivalent nature of the nitro-stabilized anions, permitting both C and O alkylations.

There is a lack of convenient methods for the preparation of these furan and isoxazoline derivatives. The general strategy for synthesis of these five-membered nitronates (isoxazoline-2-oxides) involves cyclization of γ-functionalized nitro compounds (Kunetsky, R. A.; et al. *Synthesis* 2006, 13, 2265; Kunetsky, R. A.; et al. *Org. Lett.* 2003, 5, 4907), which themselves require tedious preparation. An alternative synthesis involves [3+2]cycloaddition of nitrile oxides with olefins (Torssell, K. B. G. *Nitrile Oxides, Nitrones and Nitronates in Organic Synthesis*; Feuer, H., Ed.; VCH: Weinheim, 1988; pp 55-74), which suffers from rapid dimenization of nitrile oxides to form furoxan N-oxide (Whitney, R. A.; Nicholas, E. S. *Tetrahedron Lett.* 1981, 35, 3371). As such, new methods are needed to prepare furan and isoxazoline derivative.

SUMMARY OF THE INVENTION

Disclosed is a method of generating stereospecific heterocyclic compounds through desymmetrization of a cyclic dienic derivative with a stereospecific hydrolase. The stereospecific heterocyclic compounds may alternatively be generated by cyclizing a starting cyclic dienic compound with a Pd catalyst in the presence of a base and desymmetrizing the resultant compound with a stereospecific hydrolase. In certain embodiments, the stereospecific hydrolase is a lipase, such as *Candida antarctica* lipase B. The starting cyclic dienic derivative is, in most instances, a meso-diacetate, like furan, dicyclopentadiene, and isoxazoline-2-oxide. In specific embodiments, the cyclic dienic derivative is generated by treating a cyclic dienic compound under cyclization reaction conditions with a Pd catalyst in the presence of a base, such as sodium hydroxide, potassium carbonate, and potassium tert-butoxide. The Pd catalyst is typically a Pd(0) catalyst, such a Pd[P($C_6H_5$)$_3$]$_4$ and Pd$_2$($C_{17}H_{14}O$)$_3$.

In specific embodiments, the disclosed method also thermally decomposes the cyclic dienic compound, followed by oxidizing the decomposed cyclic dienic compound, and acetylating the oxidized dienic compound. The method uses acetic anhydride in some embodiments to acetylate the oxidized dienic compound. The dienic compound is oxidized using peracetic acid in certain embodiments. The stereospecific heterocyclic compound is treated in some embodiments with acetic anhydride followed by palladium tetrakistriphenylphosphine and potassium carbonate.

Also disclosed is a method of generating dihydrofuran compounds through cyclizing a starting cyclic dienic compound with a Pd catalyst in the presence of a base, desymmetrizing the resultant compound with a stereospecific hydrolase, converting the desymmetrized compound to a ketone, alkylating the ketone with a Pd(0) catalyst, and converting the alkylated ketone to an isoxazoline-2-oxide using a Pd(0) catalyst. In some embodiments, the desymmetrized compound is converted to a ketone using pyridinium chlorochromate and sodium acetate. The ketone is treated with alkyl lithium thereby generating cis diols. In certain embodiments, the Pd catalyst is selected from the group consisting of $Pd[P(C_6H_5)_3]_4$ and $Pd_2(C_{17}H_{14}O)_3$. The stereospecific hydrolase is *Candida antarctica* lipase B in specific embodiments.

In some embodiments, the cis diols are treated with acetic anhydride thereby generating monoacetate, followed by alkylating the monoacetate using a Pd catalyst. The conversion of alkylated ketone to an isoxazoline-2-oxide further includes treating the monoacetate with potassium carbonate and palladium tetrakistriphenylphosphine in some embodiments.

The involvement of the heteroatom in the alkylation leading to the substituted furan, lactams, isoxazoline, and other ring systems provides opportunities for exploiting the palladium catalyzed reaction in synthesis of these and other important heterocyclic systems. The versatility of Pd catalyzed cyclizations was analyzed, finding stereoselective synthesis of several new furan and isoxazoline derivatives under mild reaction conditions.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
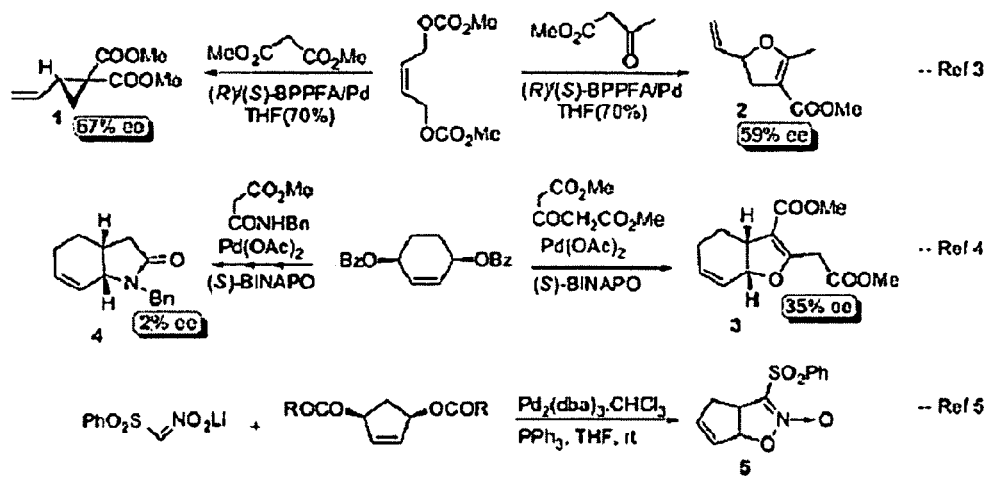
FIG. 1 is an illustrative diagram of furans and isoxazoline-2-oxide reaction equations.
Figure 2:
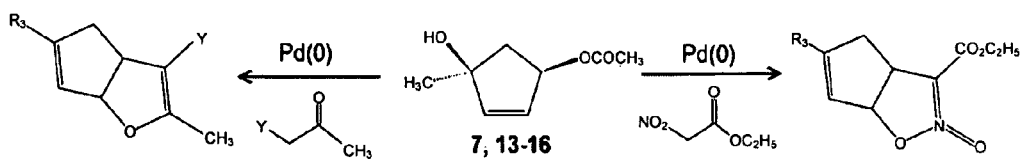
FIG. 2 is an illustrative diagram of isoxazoline-2-oxides and furan analog reactions using Pd-catalyzed cyclization.

The syntheses of furan and isoxazoline-2-oxide analogs, seen in FIG. 2, were achieved by an intramolecular Pd(0) catalyzed cyclization and also involves enzymatic desymmetrization of meso starting materials. The synthetic approach described herein brings the best of both (chemical and enzymatic) approaches in organic synthesis.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number of carbon atoms. Alkyl groups may be straight, or branched. Non-limiting examples of an "alkyl" include methyl, ethyl, propyl, isopropyl, butyl, iso-, sec- and tert-butyl, pentyl, hexyl, heptyl, 3-ethylbutyl, and the like.

As used herein, an "alcohol" is a compound on which a hydroxyl group is bound to a carbon atom of an alkyl or substituted alkyl group, which may act as a nucleophile as is known in the art, due to lone pairs of electrons on the oxygen of the hydroxyl group. Alcohols possessing short alkyl chains may be used as a protic solvent due to hydrogen bonding of its hydroxyl group, thereby promoting or enhancing solute solubility in water. The hydroxyl group also allows the alcohol to behave as a weak acid via deprotonation, or as a base. Oxidation of the alcohol results in an aldehyde, ketone or carboxylic acid, and can undergo nucleophilc substitution to form an ester compound. Alcohols may undergo E1 elimination reaction to produce alkenes.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl, phenyl, naphthyl, and anthracenyl. The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroiso-quinoline and pyrimidine. Preferred examples of heteroaryl groups include thienyl, benzothienyl, pyridyl, quinolyl, pyra-zolyl, pyrimidyl, imidazolyl, benzimidazolyl, furanyl, ben-zofuranyl, dibenzofuranyl, thiazolyl, benzothiazolyl, isox-azolyl, oxadiazolyl, isothiazolyl, benzisothiazolyl, triazolyl, pyrrolyl, indolyl, pyrazolyl, and benzopyrazolyl. [0219] When the either or both the A and B rings are substituted, the substitution may occur on either a carbon or on a heteroatom.

The term "cycloalkyl" refers to a cyclic hydrocarbon. Examples of cycloalkyl include cyclopropyl, cyclobutyl, cyclopentyl, cyclohexyl, cycloheptyl and cyclooctyl. The term "heterocycloalkyl," refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl.

The term "alkylation" means the transfer of an alkyl group from one molecule to another. Alkylation may occur through nucleophilic addition of an alkyl anion (carbanion), such as an electron-deficient carbonyl group. Alkylation may also occur through addition of an alkyl cation, like an alkyl halides with a Lewis acid catalyst.

The term "base" means a compound capable of acting as either an electron-pair donor or proton acceptor. In specific embodiments of the invention, the base is a Lewis base, thereby donating an electron-pair donor.

The term "desymmetrization" means to remove the exact corresponding structure and constituent configuration from the opposite sides of a chiral bond. A compound is deemed to possess symmetry if one half of the compound can be rotated and/or reflected onto the other.

The terms "halogen" or "halo" indicate a nonmetal element from Group 17 and include fluorine, chlorine, bromine, and iodine.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form.

As used herein "lipase" is a hydrolase enzyme, either naturally derived or synthetic, that catalyzes the hydrolysis of ester bonds in water-insoluble, lipids. A lipase acts at a specific position on the glycerol backbone of lipid substrate. A stereospecific hydrolase is a hydrolase enzyme which acts on a chiral compound to yield a single stereoisomeric product with an optical purity of at least 90%.

As used herein "stereospecific" is used to describe the outcome of a chemical reaction including at least one chiral compound that yields a single stereoisomeric product from two or more stereoisomeric reactants. The resulting single stereoisomeric product possesses optical purity of at least 90%.

As used herein "heterocyclic compounds" are organic compounds containing at least one atom of carbon and at least one non-carbon element within a ring structure. The non-carbon element may be a nonmetal, such as sulfur, oxygen or nitrogen. Non-limiting examples include pyridine ($C_5H_5N$), pyrimidine ($C_4H_4N_2$) dioxane ($C_4H_8O_2$), quinoline ($C_9H_7N$), isoquinoline ($C_9H_7N$), pyrazine ($C_4H_4N_2$), pyridazine ($C_4H_4N_2$), furan ($C_4H_4O$), tetrahydrofuran ($C_4H_8O$), and indole ($C_8H_7N$).

As used herein "cyclic dienic" compounds are organic compounds containing at least two double bonds and at least one ring moiety. Examples include, without limitation, 1,2,3,4-tetrahydroisoquinolinyl, piperazinyl, morpholinyl, piperidinyl, tetrahydrofuranyl, pyrrolidinyl, pyridinonyl, and pyrazolidinyl. Cyclic dienic derivatives are variations of cyclic dienic compounds that comprise at least one cyclic moiety with at least two functional groups. The functional groups may be, without limiting the disclosure, an alkoxy group, alkyl group, alcohol, aryl group, cycloalkyl group and halogen.

Ethyl (2R/S,1'R,4'S)-2-(4'-hydroxy-2'-cyclopenten-1'-yl)-2-nitroacetate (EHCN) and its derivatives.

Figure 3:
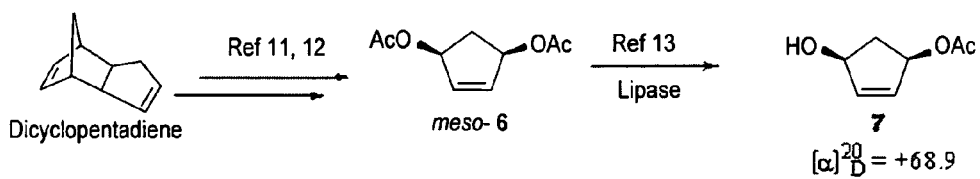
FIG. 3 is an illustration of a chemical reaction showing the formation of enantiopure (+)-monoacetate.

Commercially available dicyclopentadiene was heated to 170° C. to obtain the monomer cyclopentadiene, which was oxidized using peracetic acid to its monoepoxide (Crandall, J. K.; et al. *J. Org. Chem.* 1968, 33, 423). The monoepoxide was subsequently treated with acetic anhydride in the presence of Pd(PPh$_3$)$_4$ to obtain the meso-3,5-diacetoxycyclopentene, see compound 6 in FIG. 3. The desymmetrization of the meso-diacetate, see compound 6 in FIG. 3, with lipase to give the (+)-monoacetate, see compound 7 in FIG. 3, is the pivotal stereo-differentiation reaction.

To generate monoacetate 7, 10 g (0.054 mol) of meso-diacetate 6, was taken in a mixture of phosphate buffer (pH 7.0; 75 ml) and acetone (5 ml) in a round bottom flask. Lipase PS-30 (500 mg) was added while maintaining the pH of the reaction mixture at 7.0 using 1N NaOH solution. The reaction was stopped when no change in the pH of the reaction medium occurred. The conversion at this point was estimated to be ~60% by tlc. The reaction mixture was extracted with ethyl acetate (3×200 mL). The organic layer was dried over Na$_2$SO$_4$ and concentrated by rotoevaporation. The crude product was subjected to column chromatography over silica gel using ethylacetate:hexane (1:3) to isolate the monoacetate 7 as a white solid, mp 40-42° C.; $\alpha^D_{20}$ (CHCl$_3$)=+68.9; lit $\alpha^D_{20}$ (CHCl$_3$)=+69.6.

The desymmetrization of the meso-diacetate, unlike resolution of a racemic substrate in which the yield per enantiomer is limited to 50%, allowed conversion of higher than 97% to the enantiomerically pure single enantiomer (Deardorff, D. R.; Matthews, A. J.; McMeekin, D. S.; Craney, C. L. *Tetrahedron Lett.* 1986, 27, 1255). A simple protection/deprotection strategy would enable access to the other enantiomer.

Enzymatic asymmetric induction is a powerful tool in developing elegant synthetic methodologies for natural products (Carr, J.A.; et al. S. *Tetrahedron* 2003, 59, 9147; Bisht, K. S.; et al. *J. Org. Chem.* 1999, 64, 780). Desymmetrization of meso compounds is an extremely important reaction and involves elimination of one or more symmetry elements in the substrate. A large number of compounds including alcohols, esters, anhydrides, and nitriles have been subjected to enzymatic desymmetrizations (Garcia-Urdiales, E.; et al. *Chem. Rev.* 2005, 105, 313). Hydrolases have shown immense potential in carrying out these desymmetrizations, particularly lipases. meso-2-Cycloalken-1,4-diols and diacetates have been subjected to enzymatic desymmetrizations utilizing lipase B from *Candida antarctica* (Novo SP-435) in organic and aqueous media (Johnson, C. R.; Bis, S. J. *Tetrahedron Lett.* 1992, 33, 7287). The lipase from *Pseudomonas cepacia* (PS-30) was used to carry out hydrolytic desymmetrization of the diacetate (Siddiqi, S. M.; et al. *Nucleosides Nucleotides* 1993, 12, 267). PS-30 catalyzed reaction of meso-diacetate 6 produced monoacetate 7 in high enantiopurity (>97%) and 60% yield. Higher conversion could not be achieved even with extended reaction time. So, the recovered diacetate was again subjected to hydrolysis with the recovered enzyme to obtain enantiopure monoacetate 7 ($[\alpha]^{20}_D$+ 68.9 ($CHCl_3$); lit (Deardorff, D. R.; Matthews, A. J.; McMeekin, D. S.; Craney, C. L. *Tetrahedron Lett.* 1986, 27, 1255). ($[\alpha]^{20}_D$+69.6 ($CHCl_3$)) in total yield of 90%. The absolute stereochemistry of the monoacetate was established upon its comparison with the literature data (Deardorff, D. R.; Matthews, A. J.; McMeekin, D. S.; Craney, C. L. *Tetrahedron Lett.* 1986, 27, 1255; Johnson, C. R.; Bis, S. J. *Tetrahedron Lett.* 1992, 33, 7287) as (+)-(1S,4R)-4-acetoxylcylcopent-2-en-1-ol. The enantiopurity of monoacetate 7 was confirmed by GC analyses upon injecting racemic and enzymatically prepared monoacetate through a cyclodexB (30 m×0.25 mm, J&W scientific) chiral capillary column.

Figure 4:
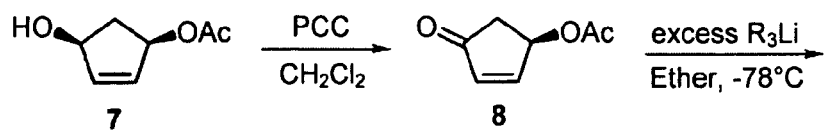
FIG. 4 is an illustration of a chemical reaction showing synthesis of monoacetates 13-16. (A) Conversion of monoacetate to cis diols. (B) The full compound reaction from starting dicyclopentadience is shown.
Figure 4:
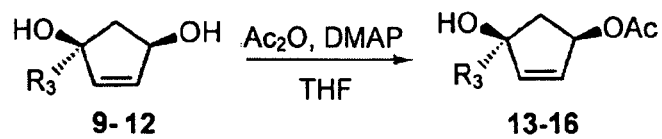
Figure 4:
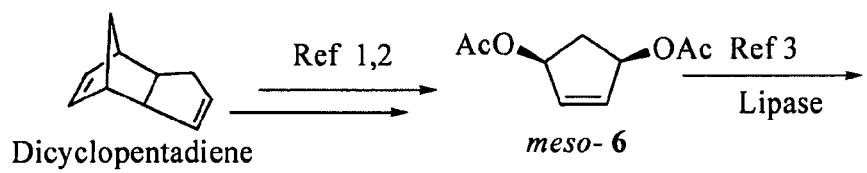
Figure 4:
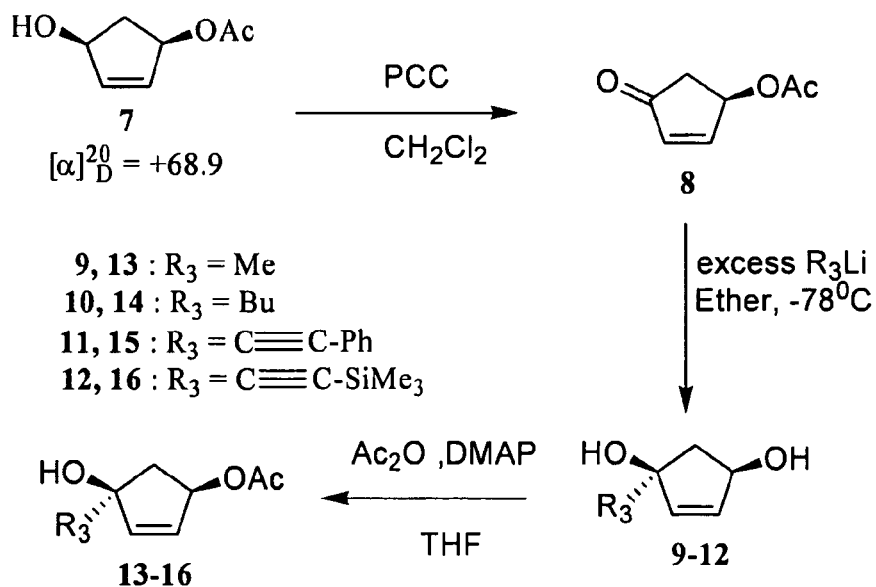

Monoacetate 7 was converted to ketone 8 using PCC (pyridinium chlorochromate) in the presence of sodium acetate in $CH_2Cl_2$, seen in FIG. 4(a) (Paquette, L. A.; et al. *Org. Synth.* 1996, 73, 36). Ketone 8 was treated with alkyl lithium to generate the cis-diols, 9-12 as the major products (>98%). To a solution of (R)-4-Acetoxy-2-cyclopenten-1-one 8 (200 mg, 1.428 mmol) in freshly distilled ether (15 ml) at −78° C. was added 1.6 M solution of methyl lithium in ether (3.57 ml, 5.712 mmol) under a nitrogen atmosphere. The reaction was allowed to stir for 1 h and was quenched using $NH_4Cl$ solution. The product was purified by column chromatography using ethyl acetate:hexane (2:1) to afford compounds 9-12 (150 mg compound 9, yield=92%) as a viscous liquid.

Figures 5, 6:
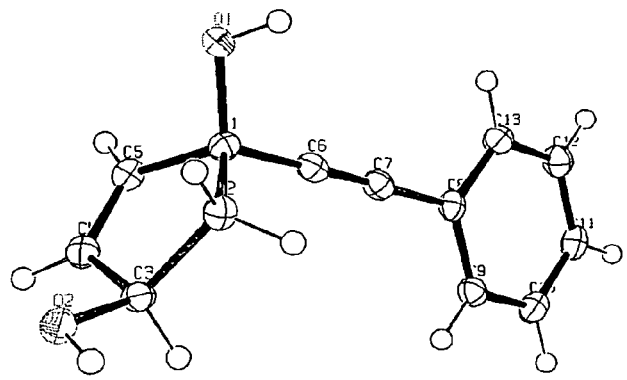
FIG. 5 is an ORTEP plot for X-ray structure of (1s, 4R)-1-Phenylethynyl-cyclopent-2-ene-1,4-diol (11).
FIG. 6 is a table of Pd(0) catalyzed alkylation, resulting in the formation of compounds 17a-p.

Spectral data for compounds 10-12 were in complete agreement with the structures and for the known compound 9, $^1H$ and $^{13}C$ spectral data were identical to that reported in the literature (Roy, A.; Schneller, S. W. *J. Org. Chem.* 2003, 68, 9269). Importantly, compound 11 produced colorless orthorhombic crystals and single crystal X-ray diffraction experimentation confirmed that the two hydroxyl groups are on the same side of the cyclopentene ring thus confirming the cis relationship, as seen in FIG. 5. The absolute stereochemistry of the molecule was also established as (1S,4R). Although diols 9, 10, and 12, did not crystallize but all had the (+)-sign of optical rotation similar to that of 11. Their absolute stereochemistry was therefore deduced as 1S,4R, identical to that of 11.

The diols thus obtained were treated with 1 mol of acetic anhydride and catalytic amount of DMAP to obtain the corresponding monoacetates (13-16), seen in FIG. 4(a), (b). To a solution of 9 (100 mg, 0.877 mmol) in dry THF (10 ml) at room temperature was added acetic anhydride (89 mg, 0.877 mmol), and catalytic amount of DMAP. The reaction was allowed to stir for 3 h and then concentrated. The residue was taken in ethyl acetate (40 ml) and was treated twice with saturated sodium bicarbonate solution (20 ml), followed by brine (10 ml). The organic layer was dried over sodium sulfate and the resulting product 13 was purified by column chromatography using ethyl acetate:hexane (1:2) (80.25 mg, yield=58.77%). The monoacetates were then coupled to the soft nucleophiles generated from the active methylene compounds, seen in FIG. 6, via Pd catalyzed alkylation to give compounds 17a-p, seen in FIG. 7.

To a solution of ethyl nitroacetate (100 mg, 0.752 mmol) or ethylacetoacetate (98 mg, 0.752 mmol) in dry THF (10 ml) at room temperature was added potassium carbonate (110 mg, 0.800 mmol) under a nitrogen atmosphere. The reaction was allowed to stir for 20 minutes and $Pd(PPh_3)_4$ (43.4 mg, 0.037 mmol), $PPh_3$ (197 mg, 0.752 mmol), monoacetate 7 (106 mg, 0.752 mmol) dissolved in 5 ml THF was added to it. The reaction was allowed to stir at 40° C. for 12 h and then vacuum filtered through celite with subsequent concentration of the filtrate. The product was purified by column chromatography using ethyl acetate:hexane (1:2) to afford 17a-h (yield ~62%).

Pd catalyzed alkylation could result in the formation of a 1,2- or 1,4-adduct (Tsuji, S. Palladium Reagents and Catalysts; Wiley: New York, N.Y., 2004; pp 431-517; Tsuji, J.; et al. *Tetrahedron Lett.* 1981, 22, 2575; Trost, B. M.; Molander, G. A. *J. Am. Chem. Soc.* 1981, 103, 5969), but under the conditions studied the reaction proceeds with high regio- and stereo-selectivity to give the 1,4 adducts, 17a-p. The stereochemistry of the Pd catalyzed allylation has been studied extensively and is known to proceed with retention of configuration via double inversion.

Figure 7:
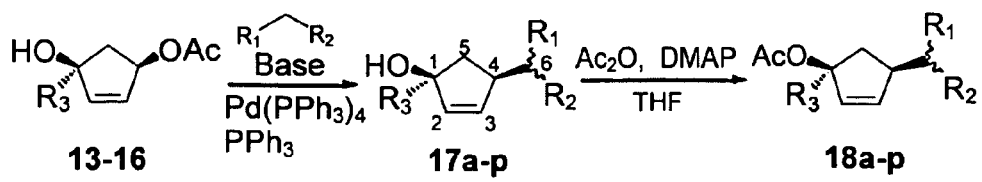
FIG. 7 is an illustration of a chemical reaction showing the synthesis of compounds 17a-p via Pd(0) catalysis.

As evident from the mechanism for these alkylations, seen in FIG. 7, compounds 17a-o would be a mixture of a pair of diastereomers at the site of the carbon-carbon bond formation (C-6). The diastereomeric ratio of 17a-o determined from integral value of the H-6, H-2, and H-3 resonances in their $^1H$ spectra was calculated to be ~1:1, seen in FIG. 6. These pairs of diastereomers were inseparable on a chromatographic column and appeared as a single spot on a TLC plate. As the diastereotopic center (C-6) is prone to racemization (because of its proximity to the electron withdrawing groups) and is involved in generation of a carbanion in the following steps, no efforts were devoted to its resolution and the mixture was taken for further steps without separation.

Acetates 18a-p were prepared by treating 17a-p with acetic anhydride in the presence of excess triethylamine and catalytic amount of DMAP. To a solution of 17a-h (100 mg, 0.465 mmol) in dry THF (10 ml) at room temperature was added acetic anhydride (51 mg, 0.5 mmol), and catalytic amount of DMAP. The reaction was allowed to stir for 3 hours and then concentrated. The residue was taken up in ethyl acetate (40 ml) and extracted twice with saturated sodium bicarbonate solution (20 ml), followed by brine (10 ml). The organic layer was dried over sodium sulfate and the resulting product 18a-h (yield~92%) was obtained. Most tertiary acetates but 18b and 18d were unstable and not amenable to purification on chromatographic columns and hence, were subjected to palladium catalyzed alkylation without any further purification.

Figure 8:
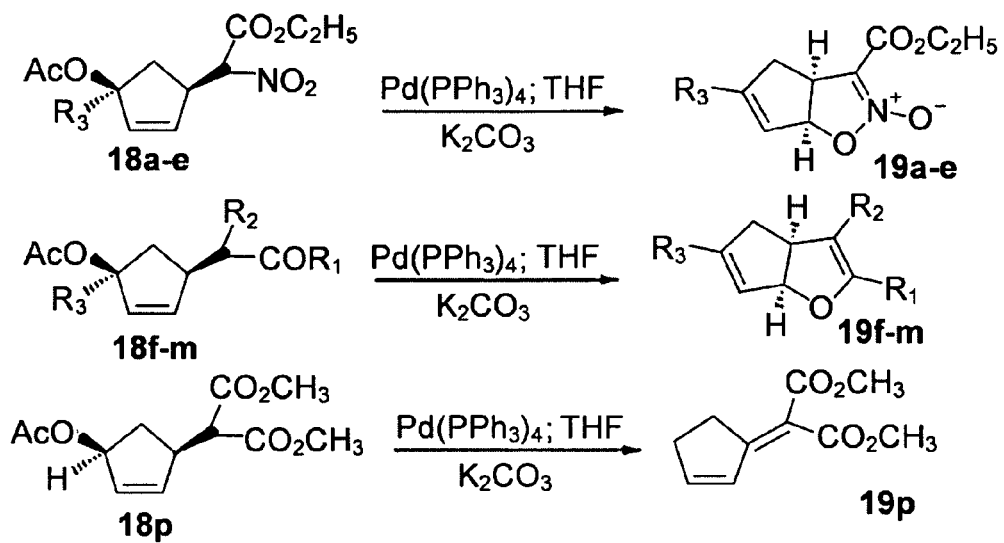
FIG. 8 is an illustration of a chemical reaction showing Pd(0) catalyzed intramolecular cyclization.
Figure 9:
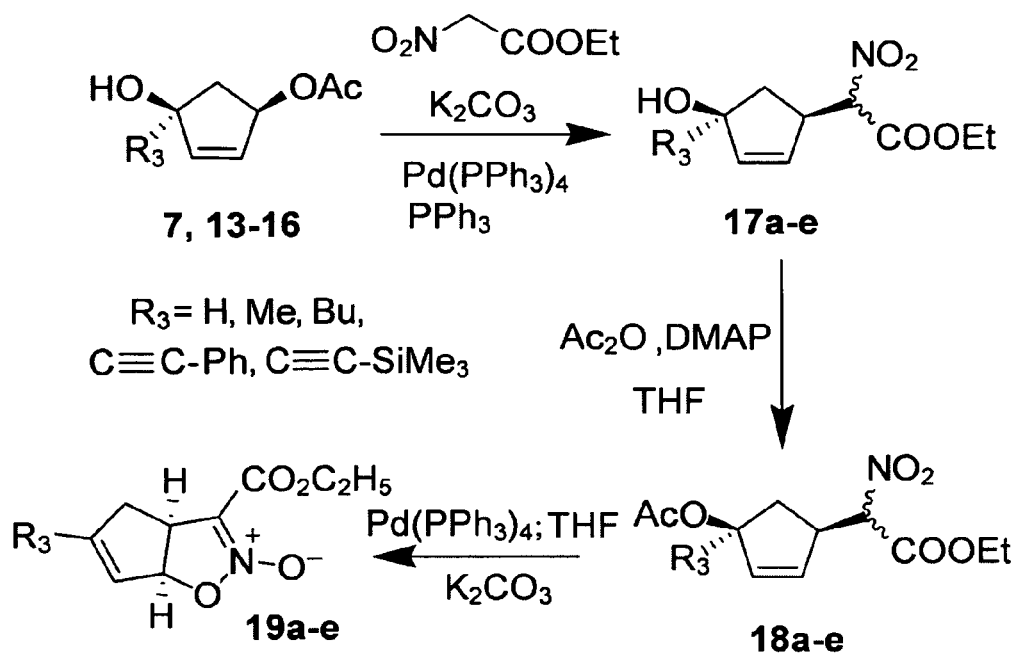
FIG. 9 is an illustration of a chemical reaction showing the synthesis of compounds 19a-e via Pd(0) catalysis.
Figure 10:
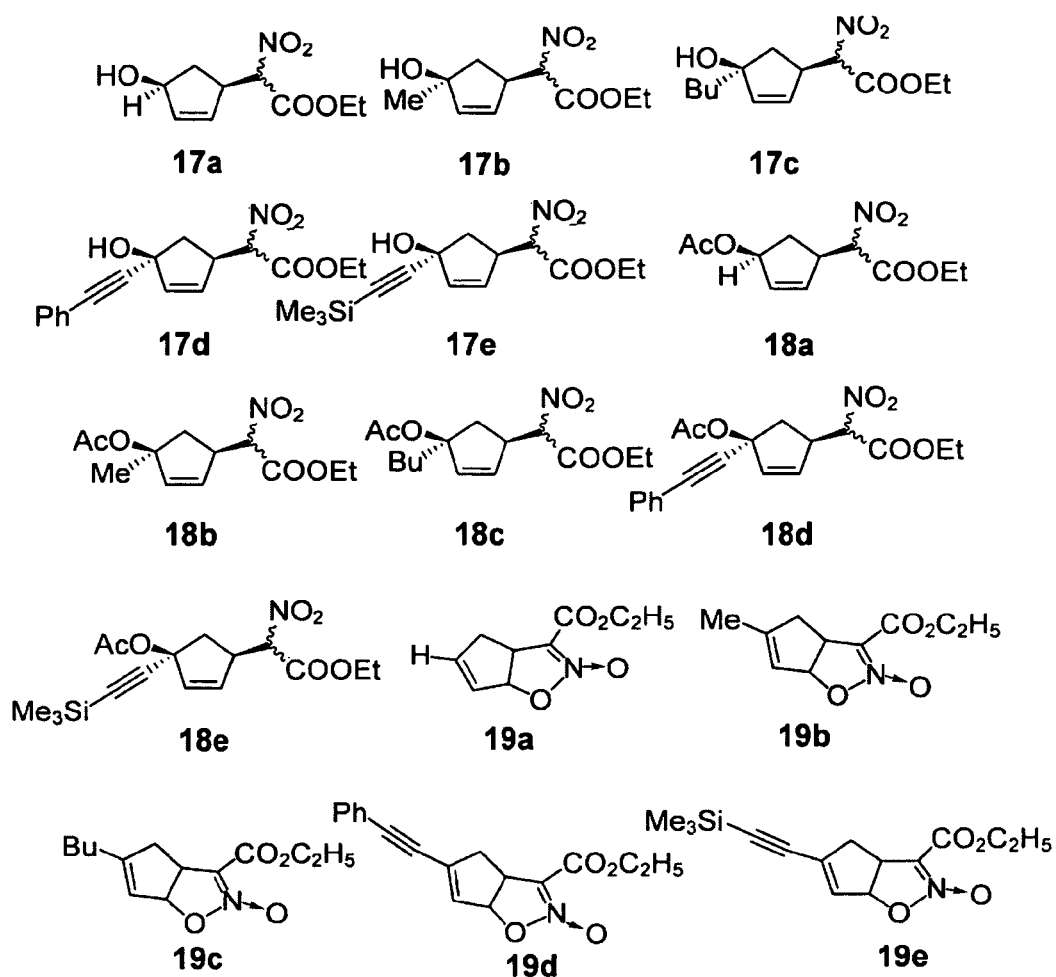
FIG. 10 depicts compounds synthesized using scheme 2, illustrated in FIG. 9.
Figure 11:
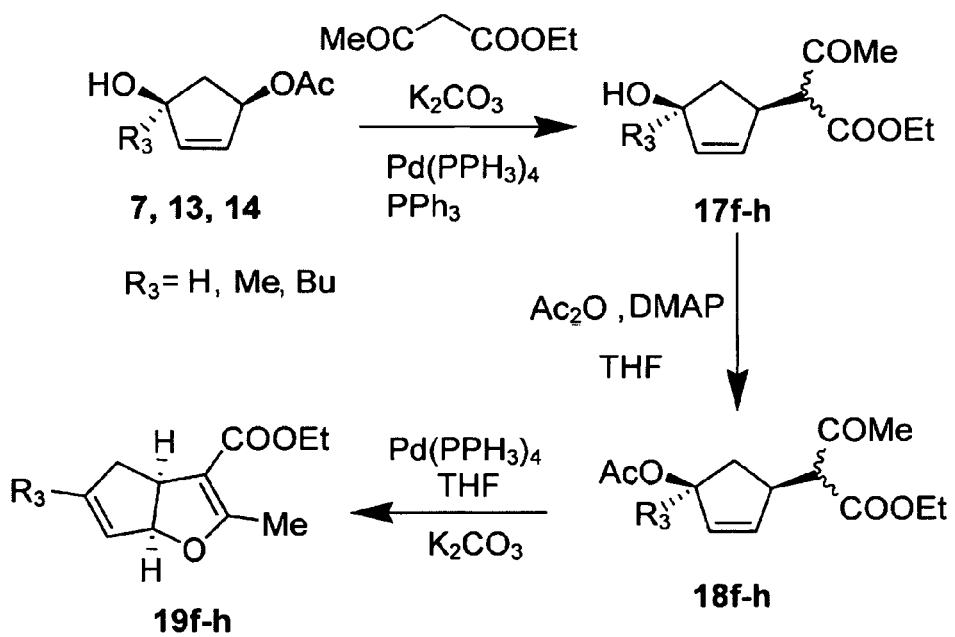
FIG. 11 is an illustration of a chemical reaction showing scheme 3, a method for synthesis of compounds 19f-h.
Figure 12:
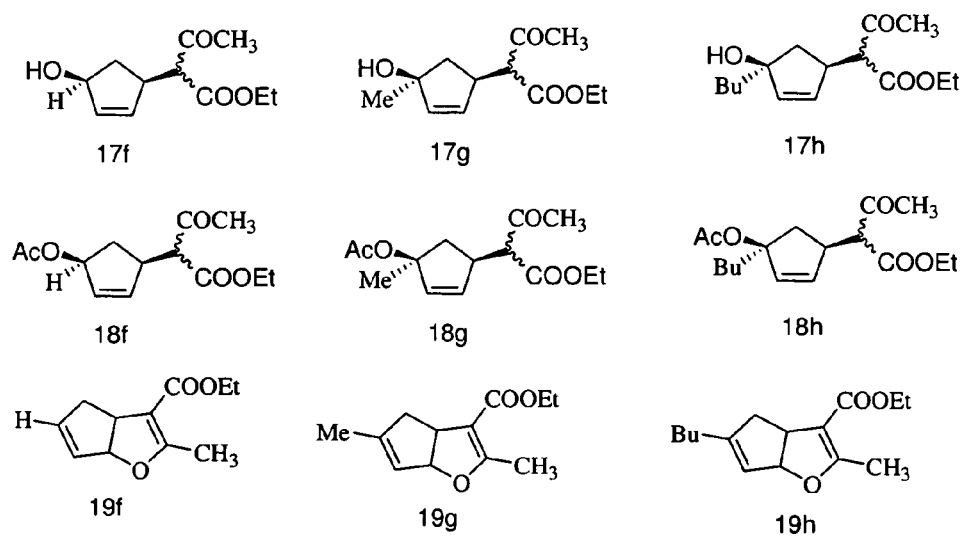
FIG. 12 depicts compounds synthesized using scheme 3, illustrated in FIG. 11.
Figure 13:
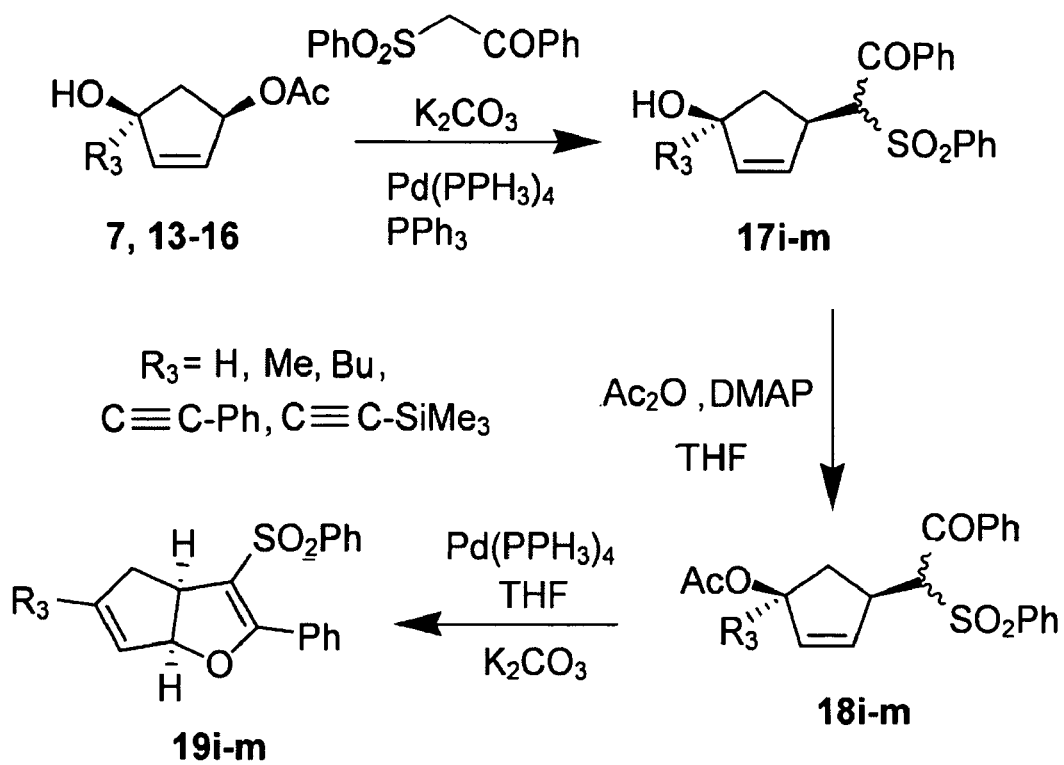
FIG. 13 is an illustration of a chemical reaction showing scheme 4, a method for synthesizing compounds 19 i-m.
Figures 14, 15:
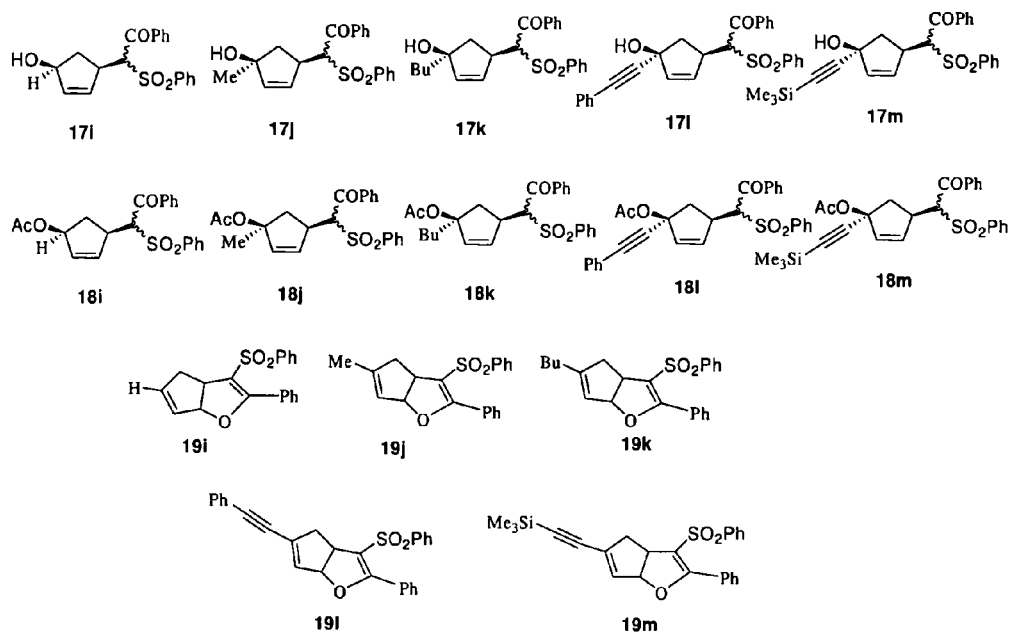
FIG. 14 depicts compounds synthesized using scheme 4, illustrated in FIG. 13.
FIG. 15 is a table of compounds 19a-m, using Pd catalyzed cyclization.

Isoxazoline-2-oxides 19a-e, seen in FIG. 10, were obtained in good to excellent yield and in optically pure form upon treating the acetates 18a-c, in presence of $K_2CO_3$ and palladium tetrakistriphenylphosphine, seen in FIGS. 8 and 9. To a solution of 18a (70 mg, 0.272 mmol) in dry THF (10 ml) at room temperature was added potassium carbonate (37.6 mg, 0.272 mmol), $Pd(PPh_3)_4$ (15 mg, 0.013 mmol). The reaction was allowed to stir for 12 h at 60° C. and then vacuum filtered over celite with subsequent concentration of the filtrate. The product was purified by wet column chromatography using ethyl acetate:hexane (1:2) to afford 19a using column chromatography as a yellow viscous liquid (45 mg, yield=85%). Similar reaction with the acetates 18f-m, seen in FIGS. 11 and 13, led to the formation of the substituted dihydrofurans 19f-m, seen in FIGS. 12 and 14, in optically pure form, seen in FIG. 15.

It is noteworthy to mention that starting from a meso-diol, optically pure compounds were prepared without utilizing chiral ligands at any stage of the reaction. The stereo-chemical outcome of the product is solely influenced by the *P. cepacia* lipase and the stereoselective nature of the palladium catalyzed transformations. Literature reports on the synthesis of the furan derivatives have been catalyzed by palladium(0) in presence of chiral ligands leading to, at best, modest enantioenrichments (Hayashi, T.; et al. *Tetrahedron Lett.* 1988, 29, 669; Yoshizaki, H.; et al. *J. Org. Chem.* 1995, 60, 2016; Tanimon, S.; et al. *Synthesis* 2006, 5, 865). The cyclization reactions were also evaluated in presence of various bases, i.e., NaH, $K_2CO_3$, and KO$^t$Bu, seen in FIG. 8, in THF using catalytic amount of Pd(0) catalysts. The yield of the reaction was independent of the base used. For all reactions recorded in FIG. 15, $K_2CO_3$ was used as the base. Pd(PPh$_3$)$_4$ and Pd$_2$(dba)$_3$ were the two Pd(0) catalysts evaluated in this reaction and identical results were obtained. Pd(II) catalysts like PdCl$_2$ did not catalyze the cyclization. The cyclizations were also attempted in absence of base or catalyst and such variations did not give the desired product indicating that both base and the catalyst are vital for this cyclization.

Figure 16:
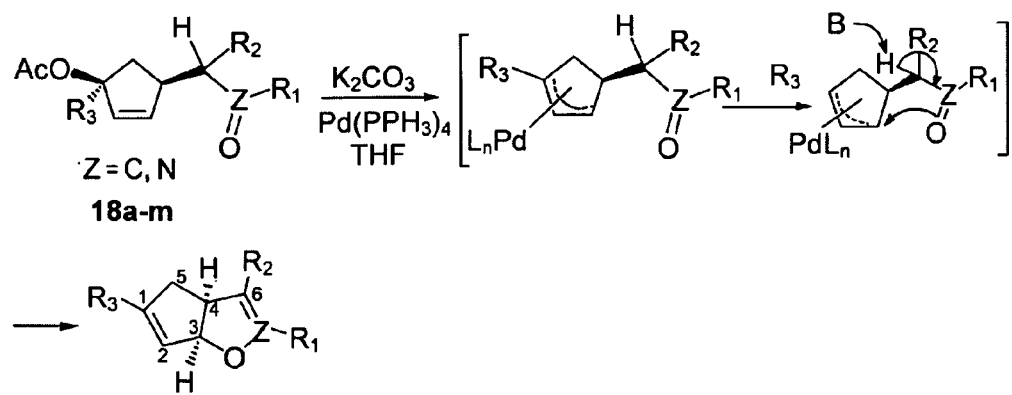
FIG. 16 is an illustration of the mechanism for formation of isoxazoline-2-oxide and furan family compounds.
Figure 17:
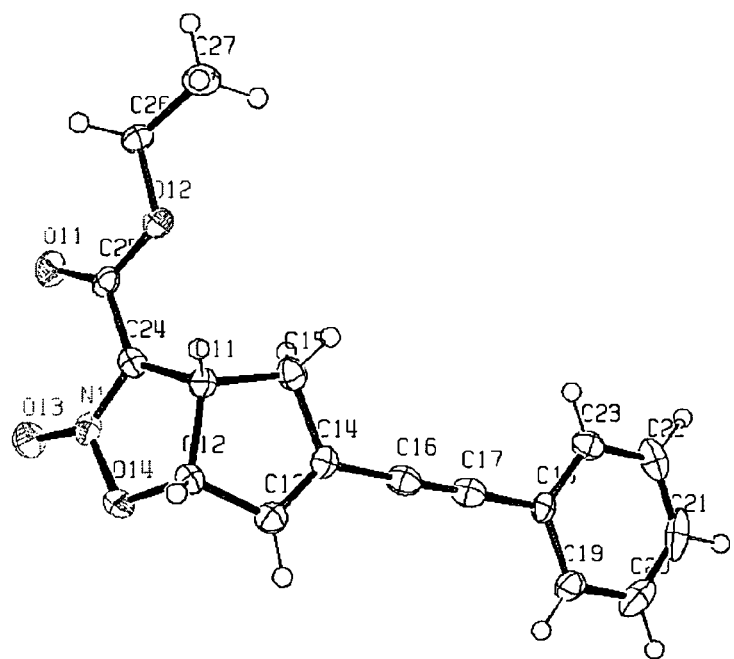
FIG. 17 ORTEP plot for X-ray structure of compound (19d).

Mechanism for formation of compounds 19a-m is shown in FIG. 16, where the base deprotonates the methine proton between the two electron-withdrawing groups. The carbanion thus generated results in the formation of 19a-m via electron-flow through NO$_2$ group (for isoxazoline-2-oxides) or enolate oxygen (for furan), seen in FIG. 16. The stereochemical outcome of the reaction is the result of two sequential steps. First is the formation of the Pd π-allyl complex formed on the opposite side of the OAc leaving group because of steric control. In the second step, the attack of the nucleophile proceed in an anti fashion with respect to metal resulting in a highly stereoselective reaction (Fiaud, J. C.; Legros, J. Y. *J. Org. Chem.* 1987, 52, 1907; Keinan, E.; Roth, Z. *J. Org. Chem.* 1983, 48, 1769). One of the isoxazoline-2-oxide 19d produced colorless orthorhombic crystals. The single crystal X-ray diffraction experiment confirmed its structure, as seen in FIG. 17. Unfortunately, the X-ray data could not establish the absolute stereochemistry of 19d but it is deduced from the stereochemistry of the monoacetate 7, as (1S,5S)-3-aza-4-(ethoxycarbonyl)-7-phenylethynyl-2-oxabicyclo[3,3.O]oct-3,7-diene-3-oxide.

Compounds 18n and 18o, containing a —CN group, did not give the desired bicyclic system; starting material was always recovered and confirmed by $^1$H NMR. In order to obtain the ee, compound 19a was treated with chiral shift-reagent, europium tris[3-(hepta-fluoropropylhydroxy-methylene)-(+) camphorate] and $^1$H NMR indicated enantiomeric excesses for compound 19a to be >97%.

Figure 18:
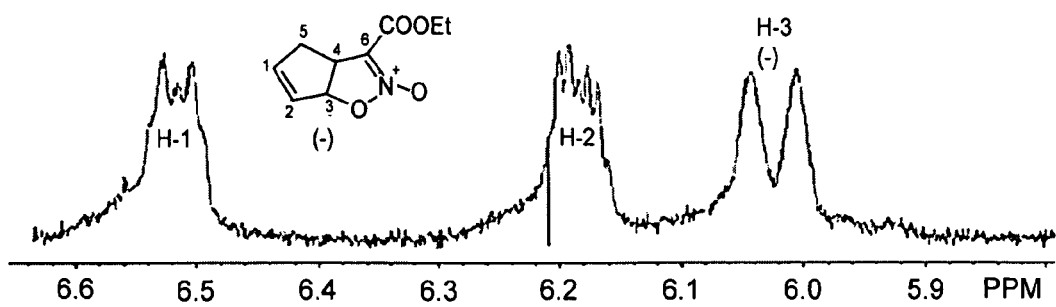
FIG. 18 is a graph of $^1$H NMR of enantioenriched compound 19a, in the presence of (+)-Eu(hfc)$_3$. The % ee was calculated using H-3 signals, where the absence of a doublet at 5.9 ppm indicates a >97% ee.
Figure 19:
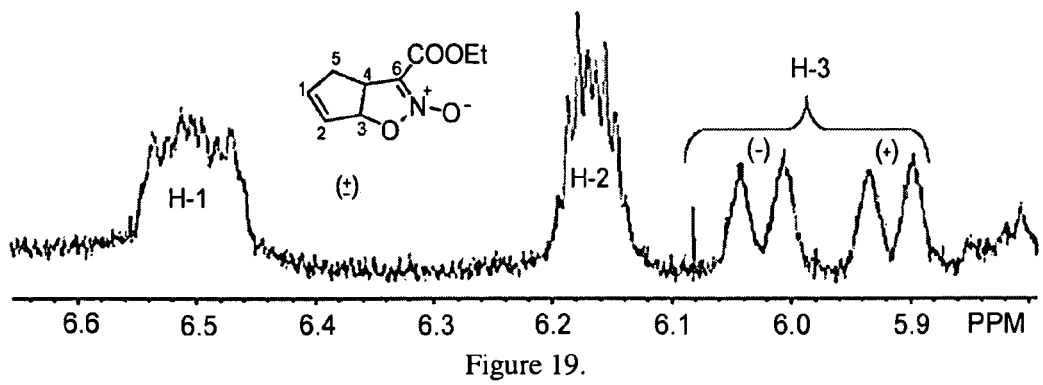
FIG. 19 is a graph of $^1$H NMR of racemic compound 19a, in the presence of (+)-Eu(hfc)$_3$. H-3 signals were used to calculate the % ee.
Figure 20:
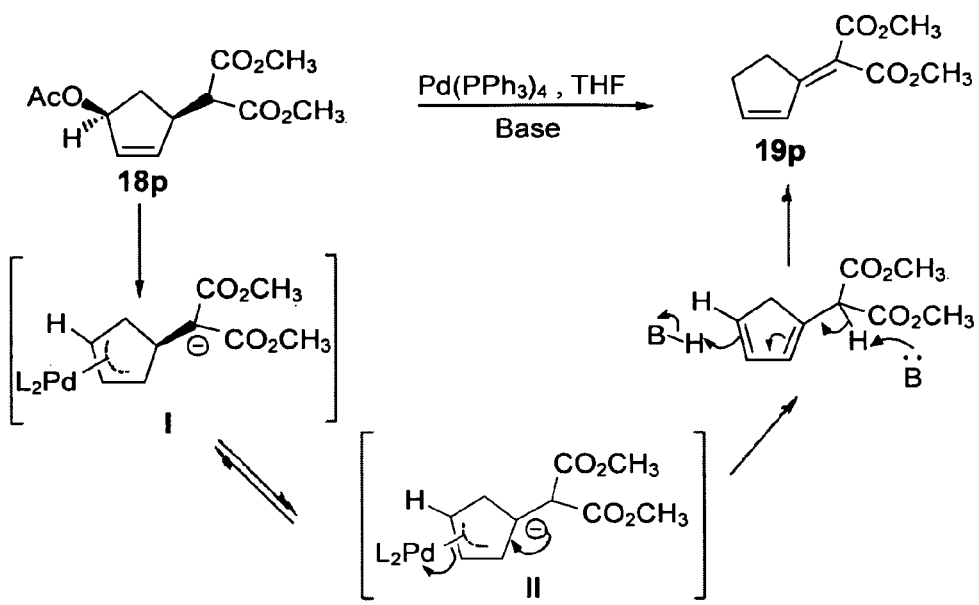
FIG. 20 shows an illustration conversion of compound 18p into compound 19p, which likely resulted form an interconversion between two π-allyl complexes, I and II.

FIGS. 18 and 19 show $^1$H NMR comparison of racemic and enantioenriched 19a in presence (+)-Eu(hfc)$_3$. The H-3 signals were used for calculation of % ee. The absence of doublet at 5.9 ppm in enantioenriched 19a indicates a >97% ee. Interestingly, compound 18p led to an unusual product 19p, which most probably results from an interconversion between the two π-allyl complexes I and II, seen in FIG. 20 (Brand, J. M.; et al. *Eu. J. Org. Chem.* 2001, 1009).

Figure 21:
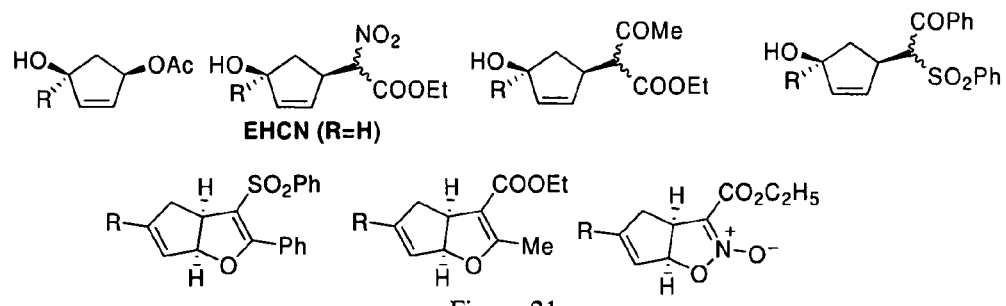
FIG. 21 depicts representative structures of Ethyl (2R/S, 1'R,4'S)-2-hydroxy-2'-cyclopenten-1'-yl)-2-nitroacetate and derivatives (EHCN). EHCN was synthesized using Pd(0) catalyzed alkylaion of a meso-diacetate using *Pseudomonas cepacia* lipase. The reaction occurs without the use of chiral ligands.

Pd catalyzed cyclization, to obtain optically pure furan and isoxazoline-2-oxide analogs, is practical, and utilizes mild reaction conditions. The method involves tandem use of the enzymatic and chemical catalysis. The key step is the desymmetrization of the meso diacetate (6) using commercially available *P. cepacia* lipase (PS-30), in high ee. This work provides a novel pathway to obtain optically pure furan and isoxazoline-2-oxide analogs, such as those seen in FIG. 21, which are rather difficult to obtain via previous strategies.

$^1$H NMR and $^{13}$C NMR spectra were recorded on a Bruker 250 MHz spectrometer and Varian 400, 500 MHz in CDCl$_3$ and acetone-d$_6$ with TMS as the standard. Chemical shifts are reported in parts per million, multiplicities are indicated by s (singlet), d (doublet), t (triplet), q (quartet), p (quintet), h (sextet), m (multiplet) and br s (broad singlet). Optical rotations were measured with a Rudolph Research Analytical AutoPol IV Automatic polarimeter. Thin-layer chromatography (TLC) was performed on glass plates coated with 0.25 mm thickness of silica gel. All solvents were dried and distilled prior to use and organic solvent extracts dried over Na$_2$SO$_4$. Mass calculations were carried out on an ESI LC MS system (Agilent Technologies). GC studies were carried out on Shimadzu gas chromatogram (Model 17A). A cyclodextrin column (30 m×0.25 mm) from J&W Scientific was used for determining the ee of the monoacetate 7.

Single-crystal X-ray diffraction data for the compounds 11 and 19d were collected on a Bruker SMART-APEX CCD Diffractometer with Kyroflex Low Temperature System using Mo Kα radiation (λ=0.7 1073 Å), operating in the Ω and φ scan mode. Diffracted data were corrected for absorption using the SADABS program.

Example 1

(+)-(1S,4R)-4-Acetoxylcylcopent-2-en-1-ol (7) (Crandall, J. K.; et al. *J. Org. Chem.* 1968, 33, 423; Deardorff, D. R.; Matthews, A. J.; et al. *Tetrahedron Lett.* 1986, 27, 1255).

meso-Diacetate 6 (Siddiqi, S. M.; et al. *Nucleosides Nucleotides* 1993, 12, 267), (10 g, 0.054 mol) was taken in a mixture of phosphate buffer (pH 7.0; 75 ml) and acetone (5 ml) in a round bottom flask. Lipase PS-30 (500 mg) was added while maintaining the pH of the reaction mixture at 7.0 using 1 N NaOH solution. The reaction was stopped when no change in the pH of the reaction medium occurred. The conversion at this point was estimated to be ~60% by TLC. The reaction mixture was extracted with ethyl acetate (3×200 mL). The organic layer was dried over Na$_2$SO$_4$ and concentrated by rotoevaporation. The crude product was subjected to column chromatography over silica gel using ethyl acetate/hexane (1:3) to isolate the monoacetate 7 as a white solid, mp 40-42° C.; $[\alpha]^{20}_D$+68.9 (CHCl$_3$); lit (Deardorff, D. R.; et al. *Tetrahedron Lett.* 1986, 27, 1255). $[\alpha]^{20}_D$+69.6 (CHCl$_3$); $^1$H NMR (CDCl$_3$, 400 MHz): δ 1.60 (dt, 1H, J=14.8, 4.0 Hz), 2.01 (s, 3H), 2.76 (p, 1H, J=7.2 Hz), 4.6 (m, 1H), 5.4 (m, 1H), 5.94 (d, 1H, J=4.0 Hz), 6.06 (m, 1H) ppm; $^{13}$C NMR (CDCl$_3$, 100 MHz): δ 20.5, 40.4, 74.6, 77.2, 132.3, 139.1, 171.3 ppm.

Example 2

(R)-4-Acetoxy-2-cyclopenten-1-one (8) (Paquette, L. A.; et al. *Org. Synth.* 1996, 73, 36)

Viscous liquid; $^1$H NMR (CDCl$_3$, 250 MHz): δ 2.03 (s, 3H), 2.22 (dt, 1H, J=18.7, 2.2 Hz), 2.73 (dt, 1H, J=19.0, 6.75 Hz), 5.78 (m, 1H), 6.26 (d, 1H, J=5.7 Hz), 7.5 (m, 1H) ppm; $^{13}$C NMR (CDCl$_3$, 62.5 MHz): δ 20.8, 40.9, 71.9, 136.9, 158.9, 170.4, 204.8 ppm.

Example 3

General Procedure for Preparation of Compounds 9-12

To a solution of (R)-4-acetoxy-2-cyclopenten-1-one 8 (200 mg, 1.428 mmol) in freshly distilled ether (15 ml) at −78° C.

was added 1.6 M solution of methyl lithium in ether (3.57 ml, 5.712 mmol) under a nitrogen atmosphere. The reaction was allowed to stir for 1 h and was quenched using NH$_4$Cl solution. The product was purified by column chromatography using ethyl acetate/hexane (2:1) to afford 9 (150 mg, yield=92%) as a viscous liquid.

(1S,4R)-1-Methylcyclopent-2-ene-1,4-diol (9).

Viscous liquid; $[\alpha]_D$+55.2 (c 0.02, acetone); $^1$H NMR (CDCl$_3$, 250 MHz): δ 1.27 (s, 3H, CH$_3$), 1.71 (dd, 1H, J=14.5, 2.7 Hz), 2.29 (dd, 1H, J=14.5, 7.2 Hz), 3.9 (br s, 2H), 4.58 (d, 1H, J=6.2 Hz), 5.79 (m, 2H) ppm; $^{13}$C NMR (CDCl$_3$, 62.5 MHz): δ 27.5, 49.5, 75.2, 81.2, 134.0, 141.0 ppm. HRESIMS calculated for C$_6$H$_{11}$O$_2$ ([M+H]$^+$): 115.0759; found: 115.0758.

(1S,4R)-1-Butyl-cyclopent-2-ene-1,4-diol (10).

Viscous liquid; $[\alpha]^{20}_D$+50.2 (c 0.03, CH$_2$Cl$_2$); $^1$H NMR (CDCl$_3$, 250 MHz): δ 0.81 (t, 3H, CH$_3$, J=6.7 Hz), 1.24 (m, 2H), 1.55 (m, 5H, H-4+OH), 1.60 (dd, 1H, J=5.5, 3.2 Hz), 2.03 (s, 1H, OH), 2.31 (dd, 1H, J=14.2, 7.0 Hz), 4.60 (d, 1H, J=5.5 Hz), 5.83 (m, 2H) ppm; $^{13}$C NMR (CDCl$_3$, 62.5 MHz): δ 14.0, 23.0, 26.5, 40.1, 48.2, 75.4, 84.1, 135.0, 140.0 ppm. HRESIMS calcd for C$_9$H$_{17}$O$_2$ ([M+H]$^+$): 157.1229; found: 157.1221.

(1S,4R)-1-Phenylethynyl-cyclopent-4-ene-1,4-diol (11)

White solid: mp=114-116° C.; $[\alpha]^{33}_D$+330.5 (c 0.11, acetone); $^1$H NMR (CDCl$_3$, 250 MHz): δ 1.97 (s, 1H, OH), 2.00 (s, 1H, OH), 2.04 (dd, 1H, J=14.0, 3.2 Hz), 2.82 (dd, 1H, J=14.0, 6.7 Hz), 4.78 (dd, 1H, J=6.7, 3.2 Hz), 6.01 (s, 2H), 7.26-7.32 (m, 5H) ppm; $^{13}$C NMR((CD$_3$)$_2$CO, 62.5 MHz): δ 52.4, 75.0, 76.2, 83.3, 93.3, 123.9, 129.1, 129.3, 132.2, 136.9, 137.7 ppm. HRESIMS calcd for C$_{13}$H$_{13}$O$_2$ ([M+H]$^+$): 201.0916; found: 201.0921.

X-ray crystallographic data for (11).

In the crystal of (1S,4R)-1-phenylethynyl-cyclopent-4-ene-1,4-diol, four molecules were found in each unit cell. The compound crystallized in an orthorhombic space group P2(1), with cell dimensions a=5.3082(10) Å, b=8.4869(16) Å, c=17.005(3) Å. A total of 5642 unique reflection data were obtained to give a final R index [I>2σ(I)] of R1=0.0337, wR2=0.0894 and R indices (all data) R1=0.0365, wR2=0.0918.

TABLE 1

| | |
|---|---|
| Identification code | kb0725 |
| Empirical formula | C$_{13}$H$_{12}$O$_2$ |
| Formula weight | 200.23 |
| Temperature | 100(2) K |
| Wavelength | 0.71073 Å |
| Crystal system | Orthorhombic |
| Space group | P2(1)2(1)2(1) |
| Unit cell dimensions | a = 6.2734(9) Å   α = 90°. |
| | b = 7.6864(11) Å   β = 90°. |
| | c = 22.307(3) Å   γ = 90°. |
| Volume | 1075.6(3) Å$^3$ |
| Z | 4 |
| Density (calculated) | 1.236 Mg/m$^3$ |
| Absorption coefficient | 0.083 mm$^{-1}$ |
| F(000) | 424 |
| Crystal size | 0.30 × 0.20 × 0.12 mm$^3$ |
| Theta range for data collection | 1.83 to 25.10°. |
| Index ranges | −7 <= h <= 7, −9 <= k <= 7, −26 <= l <= 22 |
| Reflections collected | 5642 |
| Independent reflections | 1900 [R(int) = 0.0306] |
| Completeness to theta = 25.10° | 99.7% |
| Absorption correction | SADABS |
| Max. and min transmission | 1.000 and 0.761 |

TABLE 1-continued

| | |
|---|---|
| Refinement method | Full-matrix least-squares on F$^2$ |
| Data/restraints/parameters | 1900/0/141 |
| Goodness-of-fit on F$^2$ | 0.872 |
| Final R indices [I > 2sigma(I)] | R1 = 0.0337, wR2 = 0.0894 |
| R indices (all data) | R1 = 0.0365, wR2 = 0.0918 |

(1S,4R)-1-Trimethylsilanylethynyl-cyclopent-4-ene-1,4-diol (12).

Viscous liquid; $[\alpha]^{20}_D$+278.2 (c 0.03, CH$_2$Cl$_2$); $^1$H NMR (CDCl$_3$, 250 MHz): δ 0.23 (s, 9H), 1.90 (br s, 1H, OH), 1.94 (dd, 1H, J=14.2, 3.5 Hz), 2.47 (s, 1H, OH), 2.72 (dd, 1H, J=14.2, 7.0 Hz), 4.72 (m, 1H), 5.91 (d, 1H, J=5.5 Hz), 5.97 (dd, 1H, J=5.5, 2.0 Hz) ppm; $^{13}$C NMR (CDCl$_3$, 62.5 MHz): 6-0.5, 50.6, 75.0, 75.6, 85.3, 105.8, 136.5, 137.4 ppm. HRESIMS calcd for C$_{10}$H$_{17}$O$_2$Si ([M+H]$^+$): 197.0998; found: 197.0995.

Example 4

General Procedure for Preparation of Compounds (13-16)

To a solution of 9 (100 mg, 0.877 mmol) in dry THF (10 ml) at room temperature was added acetic anhydride (89 mg, 0.877 mmol), and catalytic amount of DMAP.

The reaction was allowed to stir for 3 h and then concentrated. The residue was taken in ethyl acetate (40 ml) and was treated twice with saturated sodium bicarbonate solution (20 ml), followed by brine (10 ml). The organic layer was dried over sodium sulfate and the resulting product 13 was purified by column chromatography using ethyl acetate/hexane (1:2) (80.25 mg, yield=58.77%).

(1R,4S)-4-Hydroxy-4-methyl-2-cyclopenten-1-yl acetate (13).

$^1$H NMR (CDCl$_3$, 250 MHz): δ 1.32 (s, 3H), 1.80 (dd, 1H, J=14.5, 3.5 Hz), 1.97 (s, 3H), 2.2 (br s, 1H), 2.36 (dd, 1H, J=14.5, 7.5 Hz), 5.46 (m, 1H), 5.76 (d, 1H, J=5.5 Hz), 5.92 (d, 1H, J=5.5 Hz) ppm; $^{13}$C NMR (CDCl$_3$, 62.5 MHz): δ 21.2, 27.3, 46.7, 77.6, 80.9, 130.2, 143.2, 170.8 ppm. HRESIMS calcd for C$_8$H$_{13}$O$_3$ ([M+H]$^+$): 157.0865; found: 157.0871.

(1R,4S)-4-Hydroxy-4-butyl-2-cyclopenten-1-yl acetate (14).

Viscous liquid; $^1$H NMR (CDCl$_3$, 250 MHz): δ 0.84 (t, 3H, J=6.7 Hz), 1.26 (m, 4H), 1.54 (m, 2H), 1.72 (m, 2H, 1H+ OH) 1.97 (s, 3H), 2.40 (dd, 1H, J=14.7, 7.5 Hz), 5.43 (m, 1H), 5.80 (dd, 1H, J=5.5, 2.2 Hz), 5.91 (dd, 1H, J=4.7, 0.7 Hz); $^{13}$C NMR (CDCl$_3$, 62.5 MHz): δ 14.0, 21.2, 23.1, 26.4, 40.0, 45.0, 77.5, 83.8, 131.0, 142.0, 170.9 ppm. HRESIMS calcd for C$_{11}$H$_{19}$O$_3$ ([M+H]$^+$): 199.1334; found: 199.1333.

(1R,4S)-4-Hydroxy-4-phenylethynyl-2-cyclo-penten-1-yl acetate (15).

Viscous liquid; $^1$H NMR (CDCl$_3$, 250 MHz): δ 1.98 (s, 3H), 2.09 (dd, 1H, J=14.5, 3.7 Hz), 2.82 (s, 1H), 2.91 (dd, 1H, J=14.5, 7.2 Hz), 5.6 (m, 1H), 5.92 (dd, 1H, J=5.5, 2.2 Hz), 6.07 (d, 1H, J=5.5 Hz), 7.20-7.35 (m, 5H) ppm; $^{13}$C NMR (CDCl$_3$, 62.5 MHz): δ 21.2, 47.8, 76.0, 77.1, 84.5, 90.2, 122.2, 128.3, 128.6, 131.6, 132.0, 139.7, 170.9 ppm. HRESIMS calcd for C$_{15}$H$_{15}$O$_3$ ([M+H]$^+$): 243.1021; found: 243.1018.

(1R,4S)-4-Hydroxy-4-trimethylsilanylethynyl-2-cyclopenten-1-yl acetate (16).

$^1$H NMR (CDCl$_3$, 250 MHz): δ 0.20 (s, 9H), 1.99 (s, 3H), 2.02 (dd, 1H, J=14.5, 3.7 Hz), 2.50 (s, 1H, OH), 2.84 (dd, 1H, J=14.5, 7.5 Hz), 5.54 (m, 1H), 5.93 (dd, 1H, J=5.2, 2.0 Hz), 6.00 (d, 1H, J=5.5 Hz) ppm; $^{13}$C NMR (CDCl$_3$, 62.5 MHz):

δ −0.3, 21.1, 47.5, 75.4, 76.8, 85.0, 105.9, 132.6, 139.9, 170.7 ppm. HRESIMS calcd for $C_{12}H_{19}O_3Si$ ([M+Hi]$^+$): 239.1104; found: 239.1101.

Example 5

General Procedure for Preparation of Compounds 17a-p

To a solution of ethyl nitroacetate (100 mg, 0.752 mmol) in dry THF (10 ml) at room temperature was added potassium carbonate (110 mg, 0.800 mmol) under a nitrogen atmosphere. The reaction was allowed to stir for 20 min and Pd(PPh$_3$)$_4$ (43.4 mg, 0.037 mmol), PPh$_3$ (197 mg, 0.752 m×nol), and monoacetate 7 (106 mg, 0.752 mmol) dissolved in 5 ml THF was added to it. The reaction was allowed to stir at 40° C. for 12 h and then vacuum filtered through Celite with subsequent concentration of the filtrate. The product was purified by column chromatography using ethyl acetate/hexane (1:2) to afford 17a (120 mg, yield=62%) as a yellow viscous liquid.

Example 6

Ethyl (2R/S,1'R,4'S)-2-(4'-hydroxy-2'-cyclopenten-1'-yl)-2-nitroacetate (17a)

Viscous yellow liquid; $^1$H NMR (CDCl$_3$, 400 MHz): δ 1.25 (t, 3H, J=7.2 Hz), 1.57 (m, 1H), 1.92 (br s, 1H), 2.50 (m, 1H), 3.46 (t, 1H, J=2.4 Hz), 4.23 (q, 214, J=6.8 Hz), 4.79 (br 5, 1H), 5.06 (t, 1H, J=8.0 Hz), 5.74-5.83 (dd, 1H, J=6.0, 4.8 Hz), 5.95-5.97 (m, 1H); $^{13}$C NMR (CDCl$_3$, 100 MHz): δ 14.0, 36.2, 36.8, 45.4, 45.1, 63.3, 76.0, 76.3, 91.0, 91.4, 131.6, 132.0, 137.7, 137.9, 163.8, 163.9 ppm. HRESIMS calcd for $C_9H_{14}NO_5$ ([M+H]$^+$): 216.0872; found: 216.0875.

Example 7

Ethyl (2R/S,1'R,4'S)-2-(4'-hydroxy-4-methyl-2'-cyclopenten-1'-yl)-2-nitroacetate (17b)

Viscous yellow liquid; $^1$H NMR (CDCl$_3$, 250 MHz): δ 1.21 (t, 3H, J=7.5 Hz), 1.34 (s, 3H), 1.79 (dt, 1H, J=14.2, 5.0 Hz), 1.95 (br s, 1H), 2.19 (dd, 1H, J=14.2, 8.2 Hz), 3.50 (m, 1H), 4.19 (q, 2H, J=7.5 Hz), 5.03 (t, 1H, J=8.2 Hz), 5.59 (2dd, 1H, J=5.5, 2.0 Hz), 5.82 (dt, 1H, J=5.5, 2.0 Hz) ppm; $^{13}$C NMR (CDCl$_3$, 62.5 MHz): δ 13.9, 27.5, 27.6, 42.2, 42.8, 45.1, 45.5, 63.1, 82.1, 82.4, 90.6, 91.0, 129.1, 129.6, 141.8, 142.1, 163.7 ppm. HRESIMS calcd for $C_{10}H_{16}NO_5$ ([M+H]$^+$): 230.1029; found: 230.1034.

Example 8

Ethyl (2R/S,1'R,4'S)-2-(4'-hydroxy-4-butyl-2'-cyclopenten-1'-yl)-2-mtroacetate (17c)

Viscous yellow liquid; $^1$H NMR (CDCl$_3$, 250 MHz): δ 0.90 (t, 314, J=7.0 Hz), 1.2-1.4 (m, 7H, 2CH$_2$+CH$_3$), 1.61 (t, 2H, J=7.0 Hz), 1.75 (dt, 1H, J=14.2, 4.5 Hz), 1.89 (s, OH), 2.30 (dd, 1H, J=14.2, 8.2 Hz), 3.53 (m, 1H), 4.26 (q, 2H, J=7.2 Hz), 5.15 (dd, 1H, J=8.2, 6.5 Hz), 5.70 (dd, 0.5H, J=5.7, 2.0 Hz), 5.77 (dd, 0.5H, J=5.7, 2.2 Hz), 5.88 (dt, 1H, J=5.5, 2.2 Hz) ppm; $^{13}$C NMR (CDCl$_3$, 62.5 MHz): δ 13.9, 14.0, 23.0, 26.3, 40.4, 41.0, 45.2, 45.4, 63.1, 85.1, 91.1, 129.8, 130.2, 140.7, 140.9, 161.5 ppm. HRESIMS calcd for $C_{13}H_{22}NO_5$ ([M+H]$^+$): 272.1498; found: 272.1493.

Example 9

Ethyl (2R/S,1'R,4'S)-2-(4'-hydroxy-4-phenyl-ethynyl-2'-cyclopenten-1'-yl)-2 nitroacetate (17d)

Viscous yellow liquid; $^1$H NMR (CDCl$_3$, 250 MHz): δ 1.24 (dt, 3H, J=6.7, 1.0 Hz), 2.1 (m, 1H), 2.53 (d, 1H, J=2.7 Hz, OH), 2.74 (m, 1H), 3.65 (m, 1H), 4.19 (q, 2H, J=6.7 Hz), 5.06 (dd, 1H, J=9.0, 1.0 Hz), 5.79, 5.87 (2dd, 1H, J=5.5, 2.0 Hz), 6.00 (dt, 1H, J=5.5, 1.7 Hz), 7.22-7.36 (m, 5H) ppm; $^{13}$C NMR (CDCl$_3$, 62.5 MHz): δ 13.9, 43.7, 44.4, 44.9, 45.2, 63.21, 63.26, 76.5, 77.5, 85.2, 89.8, 90.6, 90.8, 122.1, 128.3, 128.7, 131.5, 131.6, 132.0, 138.8, 138.9, 163.5 ppm. HRESIMS calcd for $C_{17}H_{18}NO_5$ ([M+H]$^+$): 316.1185; found: 316.1180.

Example 10

Ethyl (2R/S,1'R,4'S)-2-(4'-hydroxy-4-trimethylsilanylethynyl-2'-cyclopenten-1'-yl)-2-nitroacetate (17e)

Viscous yellow liquid, $^1$H NMR (CDCl$_3$, 250 MHz): 00.19 (s, 9H), 1.21 (t, 3H, J=7.0 Hz, CH$_3$), 1.93 (m, 1H), 2.50 (s, 1H, OH), 2.74 (m, 1H), 3.62 (m, 1H), 4.20 (q, 2H, J=6.7 Hz, CH$_2$), 5.03 (dd, 1H, J=9.0, 1.0 Hz), 5.75-5.81 (2dd, 1H, J=5.5, 2.0 Hz), 6.01 (dt, 1H, J=5.5, 1.7 Hz) ppm; $^{13}$C NMR (CDCl$_3$, 62.5 MHz): 6 −0.2, 14.0, 42.7, 44.2, 60.5, 72.3, 75.4, 85.2, 90.8, 132.6, 148.1, 167.3 ppm. HRESIMS calcd for $C_{14}H_{22}NO_5Si$ ([M+H]$^+$): 312.1267; found: 312.1264.

Example 11

Ethyl (2R/S,1'R,4'S)-2-(4'-hydroxy-2'-cyclopenten-1'-yl)-3-oxobutanoate (17f)

Viscous yellow liquid; $^1$H NMR (CDCl$_3$, 250 MHz): δ 1.18 (t, 3H, J=7.2 Hz), 1.28 (t, 1H, J=7.0 Hz), 2.18 (s, 3H), 2.37 (p, 1H, J=7.2 Hz), 3.19 (m, 1H), 3.45 (m, 1H), 4.14 (q, 2H, J=7.2 Hz), 4.6 (m, 1H), 5.67-5.83 (m, 2H) ppm; $^{13}$C NMR (CDCl$_3$, 62.5 MHz): δ 14.2, 29.7, 29.9, 37.2, 37.8, 43.1, 43.2, 61.0, 64.7, 65.1, 76.22, 76.28, 134.2, 134.6, 135.2, 135.5, 168.7, 169.0, 202.61, 202.66 ppm. HRESIMS calcd for $C_{11}H_{17}O_4$ ([M+H]$^+$): 213.1127; found: 213.1134.

Example 12

Ethyl (2R/S,1'R,4'S)-2-(4'-hydroxy-4-methyl-2'-cyclopenten-1'-yl)-3-oxobutanoate (17g)

Viscous yellow liquid; $^1$H NMR (CDCl$_3$, 250 MHz): δ 1.20 (t, 3H, J=7.0 Hz), 1.29 (s, 3H), 1.50-1.71 (2dd, 1H, J=14.0, 5.2 Hz), 2.16 (m, CH$_3$+H-5), 2.55 (br s, 1H, OH), 3.24 (m, 1H), 3.47 (dd, 1H, J=8.7, 3.0 Hz), 4.13 (q, 2H, J=7.0 Hz), 5.52-5.62 (2dd, 1H, J=5.2, 2.5 Hz), 5.7 (dd, 1H, J=5.5, 2.0 Hz) ppm; $^{13}$C NMR(COGS, 62.5 MHz): δ 14.0, 27.5, 29.6, 30.0, 43.3, 43.5, 43.6, 44.2, 61.4, 64.1, 64.2, 82.2, 82.3, 131.8, 132.3, 139.7, 140.0, 168.8, 169.1, 202.3 ppm. HRESIMS calcd for $C_{12}H_{19}O_4$ ([M+H]$^+$): 227.1283; found: 227.1280.

Example 13

Ethyl (2R/S,i'R,4'S)-2-(4'-hydroxy-4-butyl-2'-cyclopenten-1'-yl)-3-oxobutanoate (17h)

$^1$H NMR (CDCl$_3$, 250 MHz): 0 0.83 (t, 3H, J=7.0 Hz), 1.21 (m, 7H, CH$_3$+2CH$_2$), 1.50 (m, 4H, 1H+CH$_2$+OH), 2.17 (m, 4H, CH$_3$+1H), 3.21 (m, 1H), 3.45 (dd, 1H, J=5.2, 3.0 Hz), 4.11 (q, 2H, J=7.0 Hz), 5.67 (m, 2H) ppm; $^{13}$C NMR (CDCl$_3$, 62.5 MHz): δ 13.0, 13.1, 22.1, 25.4, 25.6, 28.6, 29.0, 39.45, 39.47, 41.2, 41.4, 42.3, 42.5, 60.5, 63.3, 63.4, 84.1, 84.4, 132.1, 133.4, 137.1, 137.4, 167.8, 201.4 ppm. HRESIMS calcd for C$_{15}$H$_{25}$O$_4$ ([M+H]$^+$): 269.1753; found: 269.1756.

Example 14

2-Phenylsulfonyl (2R/S,1'R,4'S)-2-(4'-hydroxy-2'-cyclopenten-1'-yl)-1-phenyl-ethanone (17i)

Viscous yellow liquid; $^1$H NMR (CDCl$_3$, 250 MHz): δ 1.26-2.2 (dt, 1H, J=14.0, 4.5 Hz), 2.52 (m, 2H), 3.32 (m, 1H), 4.67-4.80 (m, 1H), 5.05 (dd, 1H, J=21.2, 9.5 Hz), 5.45-5.49 (ddd, 1H, J=5.7, 2.5, 1.0 Hz), 5.8-5.9 (dt, 1H, J=5.7, 2.5 Hz), 7.3-7.7 (m, 10H) ppm; $^{13}$C NMR (CDCl$_3$, 62.5 MHz): δ 38.2, 38.4, 43.5, 44.0, 74.0, 74.3, 75.7, 128.7, 128.8, 128.9, 129.7, 129.8, 133.7, 134.0, 134.2, 134.6, 136.2, 137.1, 137.17, 192.9, 193.3 ppm. HRESIMS calcd for C$_{19}$H$_{19}$O$_4$S ([M+H]$^+$): 343.1094; found: 343.1097.

Example 15

2-Phenylsulfonyl (2R/S,1'R,4'S)-2-(4'-hydroxy-4-methyl-2'-cyclopenten-1'-yl)-1-phenyl-ethanone (17j)

Viscous yellow liquid; $^1$H NMR (CDCl$_3$, 250 MHz): δ 1.36 (s, 3H), 1.49 (dd, 1H, J=14.0, 5.0 Hz), 2.05 (m, 1H), 2.29 (s, 1H, OH), 3.16-3.39 (m, 1H), 5.14 (dd, 1H, J=9.7, 2.5 Hz), 5.53, 5.78 (from 2 diastereomers) (2dd, 1H, J=5.5, 2.5 Hz), 6.14 (dd, 1H, J=5.2, 1.7 Hz), 7.29-7.86 (m, 10H); $^{13}$C NMR (CDCl$_3$, 62.5 MHz): δ 27.5, 29.6, 43.3, 43.5, 43.6, 44.2, 64.1, 64.2, 82.2, 82.3, 127.9, 128.4, 128.5, 128.74, 128.76, 130.1, 130.4, 131.8, 132.3, 132.6, 133.8, 180.9, 190.4 ppm. HRESIMS calcd for C$_{20}$H$_{21}$O$_4$S ([M+H]$^+$): 357.1161; found: 357.1158.

Example 16

2-Phenylsulfonyl (2R/S,1'R,4'S)-2-(4'-hydroxy-4-butyl-2'-cyclopenten-1'-yl)-1-phenyl-ethanone (17k)

Viscous yellow liquid; $^1$H NMR (CDCl$_3$, 250 MHz): δ 0.79 (t, 3H), 1.18 (m, 4H, 2CH$_2$), 1.46 (m, 3H, CH2+1H), 1.89 (s, 1H, OH), 2.01 (dd, 1H, J=13.7, 8.0 Hz), 3.40 (m, 1H), 5.15 (d, 1H, J=9.7 Hz), 5.35 (dd, 0.5H, J=5.5, 1.7 Hz), 5.68 (dd, 0.5H, J=5.5, 2.0 Hz), 5.78 (dd, 0.5H, J=5.5, 1.5 Hz), 6.23 (dd, 0.5H, J=5.7, 2.0 Hz), 7.29-7.86 (m, 10H, COPh+PhSO$_2$)ppm; $^{13}$C NMR (CDCl$_3$, 62.5 MHz): δ 12.8, 22.0, 25.3, 25.4, 39.3, 39.5, 41.5, 41.6, 42.6, 43.2, 72.9, 73.0, 83.4, 84.4, 127.73, 127.79, 127.8, 128.6, 128.7, 131.1, 132.0, 132.9, 133.1, 136.0, 136.2, 138.2, 191.9 ppm. HRESIMS calcd for C$_{23}$H$_{27}$O$_4$S ([M+H]$^+$): 399.1630; found: 399.1634.

Example 17

2-Phenylsulfonyl (2R/S,1'R,4'S)-2-(4'-hydroxy-4-phenylethynyl-2'-cyclopenten-1'-yl)-1-phenyl-ethanone (17l)

Viscous yellow liquid; $^1$H NMR (CDCl$_3$, 250 MHz): δ 1.72 (dd, 0.5H, J=14.2, 4.0 Hz), 2.47 (dd, 0.5H, J=14.2, 7.2 Hz), 2.73 (m, 2H), 3.47 (m, 1H), 5.15 (dd, 0.5H, J=15.0, 10.0 Hz), 5.49 (dd, 0.5H, J=5.2, 2.0 Hz), 5.84 (dd, 1H, J=5.2, 1.5 Hz), 5.99 (dd, 0.5H, J=5.2, 1.0 Hz), 6.47 (dd, 0.5H, J=5.2, 2.2 Hz), 7.15-7.86 (m, 15H) ppm; $^{13}$C NMR (dOd3, 62.5 MHz): δ 43.5, 44.1, 45.4, 45.7, 73.5, 73.9, 76.5, 77.4, 84.9, 85.0, 90.2, 90.4, 122.2, 122.3, 128.3, 128.3, 128.5, 128.8, 128.92, 128.97, 129.7, 129.8, 131.6, 131.7, 133.9, 134.1, 134.2, 135.1, 136.9, 137.04, 137.08, 137.2, 137.6, 192.8, 193.2 ppm. HRESIMS calcd for C$_{27}$H$_{23}$O$_4$S ([M+H]$^+$):443.1317; found: 443.1321.

Example 18

Ethyl (2R/S,1'R,4'S)-2-(4'-hydroxy-4-trimethyl-silanylethynyl-2'-cyclopenten-1'-yl).1-phenyl-ethanone (17m).

Viscous yellow liquid; $^1$H NMR (CDCl$_3$, 250 MHz): δ 0.19 (s, 9H), 1.85 (dd, 1H, J=14.2, 4.0 Hz), 2.47 (s, 1H, OH), 2.73 (m, 1H), 3.49 (m, 1H), 5.14 (d, 1H, J=10.0 Hz), 5.45 (dd, 0.5H, J=5.2, 2.0 Hz), 5.79 (dd, 0.5H, J=5.2, 1.5 Hz), 5.97 (dd, 0.5H, J=5.2, 1.0 Hz), 6.37 (dd, 0.5H, J=5.2, 2.2 Hz), 7.15-7.86 (m, 10H) ppm; $^{13}$C NMR (CDCl$_3$, 62.5 MHz): 6-0.3, 43.52, 43.56, 45.4, 45.5, 73.71, 73.74, 75.23, 75.29, 87.9, 89.0, 106.1, 106.2, 122.3, 123.0, 128.4, 128.5, 129.01, 129.08, 130.4, 133.9, 135.1, 136.1, 137.8, 140.5, 140.6, 197.5, 197.6 ppm. HRESIMS calcd for C$_{24}$H$_{27}$O$_4$SSi ([M+H]$^+$): 439.1399; found: 439.1395.

Example 19

Ethyl (2R/S,1'R,4'S)-2-(4'-hydroxy-2'-cyclo-penten-1'-yl)-2 cyanoacetate (17n)

Viscous yellow liquid; $^1$H NMR (CDCl$_3$, 250 MHz): δ 1.27 (t, 3H, J=7.7 Hz), 1.5 (tt, 1H, J=14.2, 4.0 Hz), 2.47 (s, 1H, OH), 2.56 (m, 1H), 3.23 (m, 1H), 3.53 (d, 1H, J=6.7 Hz), 4.2 (q, 2H, J=7.7 Hz), 4.76 (m, 1H), 5.73-5.83 (dt, 1H, J=5.5, 1.2 Hz), 5.99 (m, 1H) ppm; $^{13}$C NMR (CDCl$_3$, 62.5 MHz): δ 13.9, 36.8, 43.0, 44.5, 44.8, 62.9, 76.0, 76.1, 116.1, 116.2, 132.0, 132.4, 137.6, 137.7, 165.3, 165.4 ppm. HRESIMS calcd for C$_{10}$H$_{14}$NO$_3$([M+H]$^+$): 196.0974; found: 196.0977.

Example 20

Phenylsulfonyl (2R/S,1'R,4'S)-2-(4'-hydroxy-2'-cyclopenten-1'-yl)-2-acetonitrile (17o)

Viscous yellow liquid; $^1$H NMR (CDCl$_3$, 250 MHz): δ 1.6 (dq, 1H, J=14.0, 4.5 Hz), 2.2 (br s, 1H, OH), 2.58 (m, 1H), 3.43 (m, 1H), 3.99 (dd, 1H, J=27.2, 4.5 Hz), 4.76 (s, 1H), 5.76-6.02 (m, 2H), 7.55-7.71 (m, 5H) ppm; $^{13}$C NMR (CDCl$_3$, 62.5 MHz): δ 37.1, 38.8, 41.6, 42.2, 61.9, 62.1, 75.8, 76.2, 113.5, 113.7, 129.4, 129.8, 131.71, 131.75, 135.43, 135.47, 136.2, 136.3, 138.32, 138.35 ppm. HRESIMS calcd for C$_{13}$H$_{14}$NO$_3$S ([M+H]$^+$): 264.0694; found: 264.0688.

Example 21

2-(4-Hydroxy-cyclopent-2-enyl)-malonic acid dimethyl ester (17p)

Viscous liquid; $^1$H NMR (CDCl$_3$, 400 MHz): δ 1.33 (m, 1H, J=14.0, 4.5 Hz), 2.35 (p, 1H, J=7.6 Hz), 3.05 (m, 2H), 3.30 (t, 1H, J=7.6 Hz), 3.58 (s, 6H), 4.63 (s, 1H), 5.67 (d, 1H, J=5.2 Hz), 5.74 (s, 1H) ppm; $^{13}$C NMR (CDCl$_3$, 100 MHz): δ 37.6, 43.8, 52.6, 56.4, 76.3, 134.1, 135.9, 169.0, 169.2 ppm. HRESIMS calcd for C$_{10}$H$_{15}$O$_5$ ([M+H]$^+$): 215.0919; found: 215.0922.

Example 22

General Procedure for Preparation of Compounds (18a-p)

To a solution of 17a (100 mg, 0.465 mmol) in dry THF (10 ml) at room temperature was added acetic anhydride (51 mg, 0.5 mmol) and catalytic amount of DMAP. The reaction was allowed to stir for 3 h and then concentrated. The residue was taken up in ethyl acetate (40 ml) and extracted twice with saturated sodium bicarbonate solution (20 ml), followed by brine (10 ml). The organic layer was dried over sodium sulfate and the resulting product 18a (110 mg, yield=92%) was obtained as light yellow liquid.

Example 22

Ethyl (2R/S,1'R,4'S)-2-(4'-acetoxy-2'-cyclopenten-1'-yl)-2-nitroacetate (18a)

Viscous liquid; $^1$H NMR (CDCl$_3$, 400 MHz): δ 1.25 (t, 3H, J=7.2 Hz), 1.54 1.69 (m, 1H), 1.97 (s, 3H), 2.53-2.61 (m, 1H), 3.51 (br s, 1H), 4.25 (q, 2H, J=7.2 Hz), 4.96 (t, 1H, J=8.8 Hz), 5.58 (br s, 1H), 5.89-5.98 (m, 2H) ppm; $^{13}$C NMR (CDCl$_3$, 100 MHz): δ 14.0, 21.3, 33.2, 33.7, 44.7, 44.8, 63.3, 78.1, 78.4, 91.1, 91.3, 133.8, 134.0, 134.3, 134.7, 163.5, 170.8 ppm. HRESIMS calcd for $C_{11}H_{16}NO_6$ ([M+H]$^+$): 258.0977; found: 258.0978.

Example 24

Ethyl (2R/S,i'R,4'S)-2-(4'-acetoxy-4-methyl-2'-cyclopenten-1'-yl)-2-nitroacetate (18b)

Viscous liquid; $^1$H NMR (CDCl$_3$, 250 MHz): δ 1.21 (t, 3H, J=7.0 Hz), 1.5 (s, 3H), 1.91 (s, 3H), 2.02 (dt, 1H, J=14.2, 4.5 Hz), 2.21 (m, 1H), 3.52 (m, 1H), 4.2 (q, 2H, J=7.0 Hz), 4.99 (dd, 1H, J=9.2, 2.0 Hz), 5.71 (dd, 0.5H, J=5.5, 2.5 Hz), 5.76 (dd, 0.5H, J=5.7, 2.5 Hz), 6.13 (dt, 1H, J=5.5, 2.0 Hz) ppm; $^{13}$C NMR (CDCl$_3$, 62.5 MHz): δ 13.9, 22.0, 24.5, 24.6, 40.3, 41.0, 44.5, 45.0, 63.1, 90.1, 90.4, 90.8, 131.2, 131.6, 138.6, 138.8, 163.5, 170.4 ppm. HRESIMS calcd for $C_{12}H_{18}NO_6$ ([M+H]$^+$): 272.1134; found: 272.1131.

Example 25

Ethyl (2R/S,1'R,4'S)-2-(4'-acetoxy-4-phenyl-ethynyl-2'-cyclopenten-1'-yl)-2-nitroacetate (18d)

Viscous liquid; $^1$H NMR (CDCl$_3$, 250 MHz): δ 1.14 (dt, 3H, J=7.2, 2.0 Hz), 1.98 (s, 3H), 2.24 (m, 1H), 2.83 (m, 1H), 3.68 (m, 1H), 4.18 (dq, 2H, J=7.0, 1.5 Hz), 4.97 (dd, 1H, J=9.2, 5.5 Hz), 5.9 (m, 1H), 6.27 (dt, 1H, J=5.5, 2.0 Hz), 7.19-7.35 (m, 5H) ppm; $^{13}$C NMR (CDCl$_3$, 62.5 MHz): δ 13.9, 21.6, 41.9, 42.4, 44.4, 44.8, 63.2, 63.3, 81.9, 82.1, 86.3, 86.7, 90.5, 122.0, 128.2, 128.7, 131.8, 133.2, 133.7, 135.9, 136.2, 163.3, 169.1 ppm. HRESIMS calcd for $C_{19}H_{20}NO_6$ ([M+H]$^+$): 358.1291; found: 358.1294.

Example 26

Ethyl (2R/S,1'R,4'S)-2-(4'-acetoxy-2'-cyclopenten-1'-yl)-3-oxobutanoate (180)

Viscous liquid; $^1$H NMR (CDCl$_3$, 250 MHz): δ 1.12 (t, 3H, J=7.2 Hz), 1.4 (t, 1H), 1.96 (s, 3H), 2.18 (s, 3H), 2.9 (p, 1H, J=7.5 Hz), 3.33 (m, 2H), 4.03 (q, 2H, J=7.2 Hz), 5.5 (m, 1H), 5.81-5.82 (m, 2H) ppm; $^{13}$C NMR (CDCl$_3$, 62.5 MHz): δ 14.1, 21.2, 29.4, 29.7, 34.6, 34.7, 42.9, 43.0, 61.5, 61.6, 65.2, 65.3, 78.8, 78.9, 131.2, 131.3, 137.5, 137.6, 168.3, 170.7, 201.0, 201.9 ppm. HRESIMS calcd for $C_{13}H_{19}O_5$ ([M+H]$^+$): 255.1233; found: 255.1231.

Example 27

2-Phenylsulfonyl (2R/S,1'R,4'S)-2-(4'-acetoxy-2'-cyclopenten-1'-yl)-1-phenyl-ethanone (18i)

Viscous liquid; $^1$H NMR (CDCl$_3$, 250 MHz): δ 1.85-1.97 (s, 3H), 2.2-2.6 (m, 2H), 3.2-3.4 (m, 1H), 4.50 (dd, 1H, J=27.2, 10.2 Hz), 5.4-5.6 (m, 1H), 5.7-5.9 (dt, 1H, J=5.5, 2.2 Hz), 6.5 (m, 1H), 7.34-7.78 (m, 10H) ppm; $^{13}$C NMR (CDCl$_3$, 62.5 MHz): δ 21.1, 21.2, 34.8, 35.6, 43.1, 43.8, 60.4, 65.1, 74.0, 74.2, 76.6, 128.8, 128.83, 128.89, 128.97, 129.92, 132.5, 134.1, 134.3, 134.4, 135.9, 136.6, 136.9, 137.1, 137.6, 170.4, 170.6, 192.5, 192.9 ppm. HRESIMS calcd for $C_{21}H_{21}O_5S$ ([M+H]$^+$): 385.1100; found: 385.1103.

Example 28

Ethyl (2R/S,1'R,4'S)-2-(4'-acetoxy-2'-cyclopenten-1'-yl)-2-cyanoacetate (18n)

Viscous liquid; $^1$H NMR (CDCl$_3$, 250 MHz): δ 1.26 (t, 3H, J=7.0 Hz), 1.65 (m, 1H), 1.9 (s, 3H), 2.57 (p. 1H, J=6.5 Hz), 3.25 (m, 1H), 3.4-3.58 (2 doublets, (0.5×2H), J=6.5 Hz), 4.23 (q, 2H, J=7.0 Hz), 5.59 (m, 1H), 5.89-5.99 (m, 2H) ppm; $^{13}$C NMR (CDCl$_3$, 62.5 MHz): δ 14.0, 21.1, 33.8, 34.5, 42.7, 44.3, 62.9, 78.2, 78.3, 115.1, 133.5, 134.73, 165.1, 170.7, 170.8 ppm. HRESIMS calcd for $C_{12}H_{16}NO_4$ ([M+H]$^+$): 238.1079; found: 238.1080.

Example 29

Phenylsulfonyl (2R/S,1'R,4'S)-2-(4'-acetoxy-2'-cyclopenten-1'-yl)-2-acetomtrile (18o)

Viscous liquid; $^1$H NMR (CDCl$_3$, 250 MHz): δ 1.76-1.9 (m, 1H), 2.0 (s, 3H), 2.67 (m, 1H), 3.41 (m, 1H), 3.87-4.05 (2 doublets, 1H, J=6.25, 5.0 Hz), 5.55 (m, 1H), 5.91-6.05 (m, 2H), 7.56-7.98 (m, 5H) ppm; $^{13}$C NMR (CDCl$_3$, 62.5 MHz): δ 20.1, 32.8, 34.5, 40.5, 40.6, 60.5, 60.8, 76.9, 77.0, 111.8, 128.4, 128.5, 132.8, 133.0, 133.2, 133.5, 134.4, 134.9, 135.1, 169.7, 169.6 ppm. HRESIMS calcd for $C_{15}H_{16}NO_4S$ ([M+H]$^+$): 306.0800; found: 306.0814.

Example 30

2-(4-Acetoxy-cyclopent-2-enyl)-malonic acid dimethyl ester (18p)

Viscous liquid; $^1$H NMR (CDCl$_3$, 250 MHz): δ 1.56 (dt, 1H, J=14.0, 4.5 Hz), 2.05 Cs, 3H), 2.54 (dt, 1H, J=14.0, 8.0 Hz), 3.33 (m, 2H), 3.77 (s, 6H), 5.6 (m, 1H), 5.88 (dt, 1H, J=5.7, 2.0 Hz), 6.00 (dt, 1H, J=5.7, 2.0 Hz) ppm; $^{13}$C NMR (CDCl$_3$, 100 MHz): δ 21.0, 34.5, 43.4, 52.3, 52.4, 56.7, 78.7, 131.3, 137.2, 168.4 (splits into 2), 170.6 ppm. HRESIMS calcd for $C_{12}H_{17}O_6$ ([M+H]$^+$): 257.1025; found: 257.1029.

Example 31

General Procedure for Preparation of Compounds 19a-m and 19p

To a solution of 18a (70 mg, 0.272 mmol) in dry TFIF (10 ml) at room temperature were added potassium carbonate (37.6 mg, 0.272 mmol) and Pd(PPh$_3$)$_4$ (15 mg, 0.013 mmol). The reaction was allowed to stir for 12 h at 60 C and then vacuum filtered over Celite with subsequent concentration of the filtrate. The product was purified by wet column chromatography using ethyl acetate/hexane (1:2) to afford 19a using column chromatography as a yellow viscous liquid (45 mg, yield=85%).

Example 32

(1S,5S)-3-Aza-4-(ethoxycarbonyl)-2-oxabi-cyclo [3.3.0]oct-3,7-diene-3-oxide (19a)

Viscous liquid; $^1$H NMR (CDCl$_3$, 250 MHz): δ 1.29 (t, 3H, J=5.8 Hz), 2.63-2.78 (m, 2H), 4.17-4.28 (m, 3H, CH$_2$+H–4), 5.56-5.62 (m, 1H), 5.75-5.78 (m, 1H), 6.09-6.12 (m, 1H) ppm; $^{13}$C NMR (CDCl$_3$, 62.5 MHz): δ 14.0, 38.2, 44.6, 61.4, 84.2, 111.3, 127.7, 137.0, 158.9 ppm. HRESIMS calcd for C$_9$H$_{12}$NO$_4$ ([M+$^{14}$]$^+$): 198.0766; found: 198.0762.

Example 33

(1S,5S)-3-Aza-4-(ethoxycarbonyl)-7-methyl-2-oxa-bicycle[3.3.0]oct-3,7-diene-3-oxide (19b)

Viscous liquid; $^1$H NMR (CDCl$_3$, 400 MHz): δ 1.31 (t, 3H, J=6.8 Hz), 1.81 (s, 3H), 2.56 (d, 1H, J=17.6 Hz), 2.73 (dd, 1H, J=17.2, 8.0 Hz), 4.27 (m, 3H), 5.45 (s, 1H), 5.56 (d, 1H, J=8.8 Hz) ppm; $^{13}$C NMR (CDCl$_3$, 100 MHz): δ 14.4, 16.6, 42.6, 45.6, 61.8, 85.1, 112.1, 122.6, 148.5, 160.0 ppm. HRESIMS calcd for C$_{10}$H$_{14}$NO$_4$ ([M+H]$^+$): 212.0923; found: 212.0918.

Example 34

(1S,5S)-3-Aza-7-butyl-4-(ethoxycarbonyl)-2-oxabi-cyclo[3.3.0]oct-3,7-diene-3-oxide (19c)

Viscous liquid; $^1$H NMR (CDCl$_3$, 250 MHz): δ 0.79 (t, 3H, J=7.0 Hz), 1.20 (m, 5H, CH$_2$+CH$_3$), 1.33 (m, 2H), 2.07 (t, 2H, J=7.5 Hz), 2.53 (d, 1H, J=17.5 Hz), 2.75 (dd, 1H, J=16.0, 7.7 Hz), 4.24 (m, 3H), 5.43 (d, 1H, J=1.0 Hz), 5.33 (d, 1H, J=8.7 Hz); $^{13}$C NMR (CDCl$_3$, 62.5 MHz): δ 13.9, 13.9, 22.4, 29.6, 30.6, 42.5, 45.8, 61.5, 84.8, 112.3, 120.8, 150.3, 160.8 ppm. HRESIMS calcd for C$_{13}$H$_{20}$NO$_4$ ([M+H]$^+$): 254.1392; found: 254.1394.

Example 35

(1S,5S)-3-Aza-4-(ethoxycarbonyl)-7-phenyl-ethy-nyl-2-oxabicyclo [3.3.0]oct-3,7-diene-3-oxide (19d).

White solid: mp=72-74° C.; $^1$H NMR (CDCl$_3$, 250 MHz): δ 1.26 (t, 3H, J=7.0 Hz), 2.81-3.04 (m, 2H), 4.27 (m, 3H), 5.66 (d, 1H, J=9.0 Hz), 6.01 (d, 1H, J=2.0 Hz), 7.25-7.40 (m, 5H, Ph) ppm; $^{13}$C NMR (CDCl$_3$, 62.5 MHz): δ 14.2, 41.8, 45.0, 61.8, 83.7, 83.9, 95.5, 110.9, 122.1, 128.4, 129.0, 131.0, 131.4, 131.7, 159.0 ppm; MS (ESI) ink=298.1 [M+H]$^+$. HRESIMS calcd for C$_{17}$H$_{16}$NO$_4$ ([M+$^{14}$]$^+$): 298.1079; found: 298.1072.

X-ray crystallographic data for 19d.

For the crystal of 19d, four molecules were found in each unit cell. The compound crystallized in an orthorhombic space, group P2(1)$_2$(1)$_2$(1), with cell dimensions a=6.630(4) Å, b=10.067(6) Å, c=21.631(11) Å. A total of 3479 unique reflection data were obtained to give a final R indices [l>2σ (l)] of R1=0.0626, wR2=0.1308 and R indices (all data) R1=0.0824, wR2=0.1444.

TABLE 2

| Identification code | kb0825 |
|---|---|
| Empirical formula | C$_{17}$H$_{15}$NO$_4$ |
| Formula weight | 297.30 |
| Temperature | 100(2) K |
| Wavelength | 0.71073 Å |
| Crystal system | Orthorhombic |
| Space group | P2(1)2(1)2(1) |
| Unit cell dimensions | a = 6.630(4) Å α = 90°. |
| | b = 10.067(6) Å β = 90°. |
| | c = 21.631(11) Å γ = 90°. |
| Volume | 1443.7(15) Å$^3$ |
| Z | 4 |
| Density (calculated) | 1.368 Mg/m$^3$ |
| Absorption coefficient | 0.098 mm$^{-1}$ |
| F(000) | 624 |
| Crystal size | 0.30 × 0.07 × 0.06 mm$^3$ |
| Theta range for data collection | 1.88 to 25.01°. |
| Index ranges | −7 <= h <= 6, −11 <= k <= 8, −14 <= l <= 20 |
| Reflections collected | 3479 |
| Independent reflections | 2176 [R(int) = 0.0437] |
| Completeness to theta = 25.01° | 87.8% |
| Absorption correction | SADABS |
| Max. and min transmission | 1.000 and 0.598 |
| Refinement method | Full-matrix least-squares on F$^2$ |
| Data/restraints/parameters | 2176/0/206 |
| Goodness-of-fit on F$^2$ | 1.009 |
| Final R indices [I > 2sigma(I)] | R1 = 0.0626, wR2 = 0.1308 |
| R indices (all data) | R1 = 0.0824, wR2 = 0.1444 |
| Absolute structure parameter | 0(3) |
| Largest diff. peak and hole | 0.251 and −0.201 e · Å$^{-3}$ |

Example 36

(1S,5S)-3-Aza-4-(ethoxycarbonyl)-7-trimethylsila-nylethynyl-2-oxabicyclo[3.3.0]oct-3,7-diene-3-oxide (19e)

$^1$H NMR (CDCl$_3$, 250 MHz): δ 0.10 (s, 9H), 1.25 (t, 3H, J=7.0 Hz), 2.85-3.09 (m, 2H), 4.20 (m, 3H), 5.70 (d, 1H, J=8.7 Hz), 6.05 (d, 1H, 0.1=2.0 Hz) ppm; $^{13}$C NMR (CDCl$_3$, 62.5 MHz): δ 0.5, 14.3, 40.9, 44.5, 62.0, 82.7, 99.4, 102.0, 111.2, 128.1, 136.2, 160.0 ppm; MS (ESI) m/z=294.1 [M+H]$^+$. HRESIMS calcd for C$_{14}$H$_{20}$NO$_4$Si ([M+H]$^+$): 294.1162; found: 294.1165.

Example 37

(1S,5S)-4-(Ethoxycarbonyl)-3-methyl-2-oxabi-cyclo [3.3.0]oct-3,7-diene (19f)

Viscous liquid; $^1$H NMR (CDCl$_3$, 250 MHz): δ 1.20 (t, 3H, J=7.2 Hz), 2.09 (s, 3H), 2.3 (m, 1H), 2.6 (m, 1H), 3.7 (t, 1H, J=8.4 Hz), 4.10 (q, 2H, J=6.8 Hz), 5.53 (d, 1H, J=9.2 Hz), 5.7 (br s, 1H), 5.9 (br s, 1H) ppm; $^{13}$C NMR (CDCl$_3$, 62.5 MHz): δ 14.5, 14.6, 40.1, 43.9, 59.5, 91.9, 106.6, 128.5, 137.0, 166.4, 167.1 ppm. HRESIMS calcd for C$_H$H$_{15}$O$_3$ ([M+H]$^+$): 195.1021; found: 195.1018.

Example 38

(1S,5S)-4-(Ethoxycarbonyl)-3,7-dimethyl-2-oxabi-cyclo[3.3.0]oct-3,7-diene (19g)

Viscous liquid; $^1$H NMR (CDCl$_3$, 250 MHz): δ 1.21 (t, 3H, J=7.0 Hz), 1.71 (m, 3H), 2.09 (d, 3H, J=1.2 Hz), 2.27-2.34 (m, 1H), 2.51-2.55 (m, 1H), 3.70 (dt, 1H, J=7.7, 1.0 Hz), 4.1 (m, 2H), 5.34 (m, 1H), 5.46 (d, 1H, J=8.8 Hz) ppm; $^{13}$C NMR (CDCl$_3$, 62.5 MHz): δ 14.42, 14.48, 16.5, 44.1, 44.6, 59.2, 92.3, 106.5, 123.0, 147.8, 166.3, 167.2 ppm. HRESIMS calcd for $C_{12}H_{17}O_3$ ($[M+H]^+$): 209.1178; found: 209.1181.

Example 39

(1S,5S)-7-Butyl-4-(ethoxycarbonyl)-3-methyl-2-oxabicyclo [3.3.0]oct-3,7-diene (19h).

Viscous liquid; $^1$H NMR (CDCl$_3$, 250 MHz): δ 0.78 (t, 3H, J=7.0 Hz), 1.21 (m, 5H), 1.34 (m, 2H), 2.04 (m, 5H, CH$_3$+CH$_2$), 2.33 (dd, 1H, J=14.0, 1.0 Hz), 2.53 (dd, 1H, J=14.0, 8.0 Hz), 3.72 (m, 1H), 4.07 (m, 2H), 5.34 (d, 1H, J=1.25 Hz), 5.47 (d, 1H, J=9.0 Hz) ppm; $^{13}$C NMR (CDCl$_3$, 62.5 MHz): δ 13.8, 14.45, 14.49, 22.5, 29.6, 30.7, 42.5, 44.1, 59.2, 92.2, 106.5, 121.5, 152.2, 166.4, 167.2 ppm. HRESIMS calcd for $C_{15}H_{23}O_3$ ($[M+H]^+$): 251.1647; found: 251.1645.

Example 40

(1S,5S)-3-Phenyl-4-(phenylsulfonyl)-2-oxabi-cyclo [3.3.0]oct-3,7-diene (19i)

Viscous liquid; $^1$H NMR (CDCl$_3$, 250 MHz): δ 2.73 (dt, 1H, J=7.2, 2.2 Hz), 2.85 (p, 1H, J=2.2 Hz), 3.82 (dt, 1H, J=7.7, 5.2 Hz), 5.64 (doublet of p, 1H, J=7.2, 1.2 Hz), 5.74 (dq, 1H, J=5.7, 2.2 Hz), 6.06 (dt, 1H, J=5.7, 1.2 Hz), 7.18-7.6 (m, 10H) ppm; $^{13}$C NMR (CDCl$_3$, 62.5 MHz): δ 40.1, 46.4, 91.9, 114.4, 127.0, 127.4, 127.9, 128.7, 128.8, 129.4, 130.7, 132.6, 137.2, 142.2, 163.9, 192.3 ppm. HRESIMS calcd for $C_{19}H_{17}O_3S$ ($[M+H]^+$): 325.0898; found: 325.0892.

Example 41

(1S,5S)-7-Methyl-3-phenyl-4-(phenylsulfonyl)-2-oxabicyclo[3.3.O]oct-3,7-diene (19j)

Viscous liquid; $^1$H NMR (CDCl$_3$, 250 MHz): δ 1.76 (s, 3H), 2.58-2.90 (m, 2H), 3.84 (dt, 1H, J=7.7, 2.2 Hz), 5.41 (t, 1H, J=2.0 Hz), 5.62 (d, 1H, J=9.0 Hz), 7.19-7.60 (m, 10H, PhSO$_2$+COPh) ppm; $^{13}$C NMR (CDCl$_3$, 62.5 MHz): δ 15.5, 43.2, 46.2, 91.6, 113.3, 121.5, 125.9, 126.6, 127.7, 128.0, 128.4, 129.6, 131.5, 141.3, 147.3, 163.1 ppm. HRESIMS calcd for $C_{20}H_{19}O_3S$ ($[M+H]^+$): 339.1055; found: 339.1050.

Example 42

(1S,5S)-7-Butyl-3-phenyl-4-(phenylsulfonyl)-2-oxabicyclo[3.3.O]oct-3,7-diene (19k)

Viscous liquid; $^1$H NMR (CDCl$_3$, 250 MHz): δ 0.80 (t, 3H, J=7.2 Hz), 1.19 (m, 2H), 1.31 (m, 2H), 2.05 (t, 2H, J=7.5 Hz), 2.58-2.90 (m, 2H), 3.80 (dt, 1H, J=7.7, 2.2 Hz), 5.40 (d, 1H, J=2.0 Hz), 5.60 (d, 1H, J=9.2 Hz), 7.19-7.60 (m, 10H, PhSO$_2$+COPh) ppm; $^{13}$C NMR (CDCl$_3$, 62.5 MHz): δ 13.9, 22.4, 29.5, 30.6, 42.5, 46.7, 92.4, 114.3, 121.1, 126.9, 127.7, 128.7, 129.1, 129.4, 130.6, 132.5, 142.4, 152.7, 164.1 ppm. HRESIMS calcd for $C_{23}H_{25}O_3S$ ($[M+H]^+$): 381.1524; found: 381.1522.

Example 43

(1S,5S)-3-Phenyl-7-phenylethynyl-4-(phenylsulfonyl)-2oxabicyclo[3.3.0]oct-3,7-diene (19l).

Viscous liquid; $^1$H NMR (CDCl$_3$, 250 MHz): δ 2.89-3.17 (m, 2H), 3.94 (dt, 1H, J=8.2, 2.2 Hz), 5.70 (d, 1H, J=9.0 Hz), 6.00 (d, 1H, J=1.7 Hz), 7.26-7.61 (m, 15H); $^{13}$C NMR (CDCl$_3$, 62.5 MHz): δ 43.7, 46.6, 84.5, 91.4, 94.8, 114.3, 122.5, 127.0, 127.7, 128.4, 128.6, 128.8, 129.4, 130.8, 131.0, 131.7, 131.9, 132.0, 132.7, 142.1, 164.2 ppm. HRESIMS calcd for $C_{27}H_{21}O_3S$ ($[M+H]^+$): 425.1211; found: 425.1203.

Example 44

(1S,5S)-3-Phenyl-4-(phenylsulfonyl)-7-trimethyl-silanyl-2oxabicyclo [3.3.0]oct-3,7-diene (19m).

Viscous liquid; $^1$H NMR (CDCl$_3$, 250 MHz): δ 0.14 (s, 9H), 2.85-3.05 (m, 2H), 3.99 (dt, 1H, J=8.5, 2.0 Hz), 5.72 (d, 1H, J=9.0 Hz), 6.10 (d, 1H, J=1.7 Hz), 7.26-7.65 (m, 10H, PhSO$_2$+COPh) ppm; $^{13}$C NMR (CDCl$_3$, 62.5 MHz): δ 0.5, 43.5, 46.7, 90.5, 98.0, 102.1, 114.2, 122.7, 127.5, 128.7, 129.0, 129.6, 131.4, 133.0, 134.4, 165.0 ppm. HRESIMS calcd for $C_{24}H_{25}O_3SSi$ ($[M+H]^+$): 421.1294; found: 421.1288.

Example 45

2-Cyclopent-2-enylidene-malonic acid dimethyl ester (19p)

Viscous liquid; $^1$H NMR (CDCl$_3$, 250 MHz): δ 2.58 (m, 2H), 2.90 (m, 2H), 3.70 (s, 3H), 3.73 (s, 3H), 6.76 (s, 2H) ppm; $^{13}$C NMR (CDCl$_3$, 62.5 MHz): δ 31.0, 32.9, 51.8, 52.0, 115.3, 132.4, 152.4, 166.2, 166.6, 168.3 ppm. HRESIMS calcd for $C_{10}H_{13}O_4$ ($[M+H]^+$): 197.0814; found: 197.0812.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating neurodegenerative disease, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

What is claimed is:
1. A method of generating stereospecific heterocyclic compounds, comprising the step of:
  providing a cyclic dienic derivative, wherein the cyclic dienic derivative is a meso diacetate;
  desymmetrizing the cyclic dienic derivative with a stereospecific lipase to generate an asymmetric monoacetate, wherein the stereospecific lipase is obtained from *Pseudomonas cepacia;*
  generating a substituted cis diol from the asymmetric monoacetate, further comprising:
    converting the asymmetric monoacetate to a ketone;
    treating the ketone with an alkyl lithium, wherein the alkyl is substituted to the ketone thereby forming the substituted cis diol;

generating a substituted asymmetric monoacetate from the substituted cis diol, further comprising:
  generating a monoacetate from the substituted cis diol using acetic anhydride;
  reacting the monoacetate with a palladium (0) catalyst and an alkyl or alkene to generate a substituted alcohol;
  treating the substituted alcohol with acetate anhydride to generate the substituted asymmetric monoacetate; and
intramolecular cyclizing the asymmetric monoacetate using a palladium (0) catalyst in the presence of a base to form a stereospecific heterocyclic compound.

2. The method of claim 1, wherein the base is selected from the group consisting of sodium hydroxide, potassium carbonate, and potassium tert-butoxide.

3. The method of claim 1, wherein the Pd(0) catalyst is selected from the group consisting of $Pd[P(C_6H_5)_3]_4$ and $Pd_2(C_{17}H_{14}O)_3$.

4. The method of claim 1, further comprising: thermally decomposing a cyclic dienic compound to generate a monomer diene; oxidizing the monomer diene to generate a monoepoxide; and acetylating the monoepoxide to obtain the cyclic dienic derivative.

5. The method of claim 4, wherein the monoepoxide is acetylated using acetic anhydride.

6. The method of claim 4, wherein the monomer diene is oxidized using peracetic acid.

7. A method of generating stereospecific heterocyclic compounds, comprising the steps of:
  providing a cyclic dienic compound;
  generating a meso diacetate from the cyclic dienic compound, further comprising:
    oxidizing the cyclic dienic compound to form a monoepoxide;
    acetylating the monoepoxide with an acetate compound to form the meso diacetate;
  desymmetrizing the meso diacetate with a stereospecific hydrolase to generate an asymmetric monoacetate, wherein the stereospecific hydrolase is lipase obtained from *Pseudomonas cepacia*;
  generating a substituted cis diol from the asymmetric monoacetate, further comprising:
    converting the asymmetric monoacetate to a ketone;
    treating the ketone with an alkyl lithium, wherein the alkyl is substituted to the ketone thereby forming the substituted cis diol;
  generating a substituted asymmetric monoacetate from the substituted cis diol, further comprising:
    generating a monoacetate from the substituted cis diol using acetic anhydride;
    reacting the monoacetate with a palladium (0) catalyst and an alkyl or alkene to generate a substituted alcohol;
    treating the substituted alcohol with acetate anhydride to generate the substituted asymmetric monoacetate; and
  intramolecular cyclizing the asymmetric monoacetate using a palladium (0) catalyst in the presence of a base to form a stereospecific heterocyclic compound.

8. The method of claim 7, wherein the base is selected from the group consisting of sodium hydroxide, potassium carbonate, and potassium tert-butoxide.

9. The method of claim 7, wherein the cyclic dienic compound is selected from the group consisting of furan, dicyclopentadiene, and isoxazoline-2-oxide.

10. The method of claim 7, wherein the Pd(0) catalyst is selected from the group consisting of $Pd[P(C_6H_5)_3]_4$ and $Pd_2(C_{17}H_{14}O)_3$.

11. The method of claim 7, wherein the oxidized dienic compound is acetylated using acetic anhydride.

12. The method of claim 7, wherein the dienic compound is oxidized using peracetic acid.

13. A method of generating dihydrofuran compounds, comprising the steps of:
  providing a cyclic dienic compound;
  generating a meso diacetate from the cyclic dienic compound, further comprising:
    oxidizing the cyclic dienic compound to form a monoepoxide;
    acetylating the monoepoxide with an acetate compound to form the meso diacetate;
  desymmetrizing the meso diacetate with a stereospecific hydrolase to generate an asymmetric monoacetate, wherein the stereospecific hydrolase is lipase obtained from *Pseudomonas cepacia*;
  generating a substituted cis diol from the asymmetric monoacetate, further comprising:
    converting the asymmetric monoacetate to a ketone;
    treating the ketone with an alkyl lithium, wherein the alkyl is substituted to the ketone thereby forming the substituted cis diol;
  generating a substituted asymmetric monoacetate from the substituted cis diol, further comprising:
    generating a monoacetate from the substituted cis diol using acetic anhydride;
    reacting the monoacetate with a palladium (0) catalyst and an alkyl or alkene to generate a substituted alcohol;
    treating the substituted alcohol with acetate anhydride to generate the substituted asymmetric monoacetate;
  alkylating the asymmetric monoacetate with a Pd(0) catalyst; and
  intramolecular cyclizing the alkylated asymmetric monoacetate to form a dihydrofuran compound using a Pd(0) catalyst.

14. The method of claim 13, further comprising converting the asymmetric monoacetate to a ketone using pyridinium chlorochromate and sodium acetate.

15. The method of claim 13, wherein the ketone is treated with alkyl lithium thereby generating the cis diol.

16. The method of claim 13, wherein the cyclizing of the alkylated asymmetric monoacetate further comprises treating the alkylated asymmetric monoacetate with potassium carbonate and palladium tetrakistriphenylphosphine.

17. The method of claim 13, wherein the Pd catalyst is selected from the group consisting of $Pd[P(C_6H_5)_3]_4$ and $Pd_2(C_{17}H_{14}O)_3$.

18. The method of claim 13, wherein the base is selected from the group consisting of sodium hydroxide, potassium carbonate, and potassium tert-butoxide.

* * * * *